United States Patent [19]

Fick et al.

[11] Patent Number: 6,149,904
[45] Date of Patent: Nov. 21, 2000

[54] METHOD FOR INHIBITING TUMOR CELL GROWTH BY ADMINISTERING TO TUMOR CELLS EXPRESSING A NUCLEIC ACID ENCODING A CONNEXIN AND A PRO-DRUG

[75] Inventors: James R. Fick, Martinez, Ga.; Mark A. Israel, Belvedere, Calif.

[73] Assignee: The Regents of the University of California, Oakland, Calif.

[21] Appl. No.: 08/791,291

[22] Filed: Jan. 30, 1997

Related U.S. Application Data

[60] Provisional application No. 60/010,930, Jan. 31, 1996.

[51] Int. Cl.[7] .............................. A61K 48/00; C12N 5/00; C12N 15/00
[52] U.S. Cl. ........................ 424/93.21; 424/93.2; 514/44; 435/325
[58] Field of Search .............................. 514/44; 424/93.2, 424/93.21; 435/325

[56] References Cited

PUBLICATIONS

Marini III, F.C. et al., *Gene Therapy* 2:655 (1995).
Fick, James. et al., *Proc. Natl. Acad. Sci. USA* 92:11071 (1995).
Bechberger, J.F. et al. Abstract Molecular Biology/Biochemistry Proceedings of the American Association for Cancer Research 36:520 (1995).
Bruzzone et al. *Eur. J. Biochem.* 238(1):1–27 (1996).
Chen, T.–H. et al. *Cell Biology and Toxicology* 1:155 (1984).
Davis, L.M. et al. *Journal of Cardiovascular Electrophysiology* 6:103 (1995).
Edelman, G.M., *Biochem*, 27:3533–3543 (1988).
Eghbali et al., *Proc. Natl. Acad. Sci. USA*, 87:1328–1331 (1990).
Elfgang et al. *J. Cell Biol.* 129(3):805–817 (1995).
Fick, J. et al. *West J Med* 161:260 (1994).
Fick, J. et al. *Crit Rev Neurosurg* 4:1 (1994).
Fick, J. et al. Abstract 2515 Proceedings of the American Association for Cancer Research 36:422 (1995).
Fick, J. et al. *Crit Rev Neurosurg* 5:85 (1995).
Fishman et al., *Cell Adhesion and Communication* 3:353–65 (1995).
Hofer, A. et al. *J. Neuroscience* 16(14)4311–21 (1996).
Holder, J.W. et al., *Cancer Research*, 53:3475–3485 (1993).
Jongen, W.M.F. et al., *J. Cell Biol.*, 114:545–555 (1991).
Keane, R.W. et al., *J. Cell Biol.*, 106:1307–1319 (1988).
Koval, M. et al., *J. Cell Biol.* 130:987–95 (1995).
Lee, S.W. et al. *The Journal of Cell Biology* 118:1213 (1992).
Mesnil et al. *Proc. Natl. Acad. Sci. USA*, 93:1831–1835. (1996).
Meyer, R.A. et al., *J. Cell Biol.*, 119:179–189 (1992).
Moore, L.K. et al., *Amer. J. Physiol.* 267(5 Pt 1):C1371–C1380 (1994).
Musil, L.S. et al., *J. Cell Biol.*, 111:2077–2088 (1990).
Naus, C.C.G. et al. *Cellular and Molecular Neurobiology* 12:163 (1992).
Naus, C.C.G. et al. *Cancer Research* 52:4208 (1992).
Naus, C.C.G. et al. *Experimental Cell Research* 206:72 (1993).
Pitts, J.D. *Molecular Carcinogenesis* 11:127 (1994).
Ruch, R.J. *Annals of Clinical and Laboratory Science* 24:216 (1994).
Shinoura, N. et al., *J. Neurosurg.* 84(5):839–846 (1996).
Vitkauskas, G.V. et al. *Biochima et Biophysica Acta* 823:19 (1985).
Zhu, D. et al., *Proc. Natl. Acad. Sci. USA*, 89:10218–10221 (1992).
Zhu,D. et al., *Proc. Natl. Acad. Sci. USA*, 88:1883–1887 (1991).
Bi, W.L. et al., In vitro evidence that metabolic cooperation is responsible for the bystander effect observed with HSV tk retroviral gene therapy, *Human Gene Therapy*, 4:725–731, (1993).
Fick et al. (1995) Proced. Natl. Acad. 92, 11071–11075.
Blau et al (1995) The New England J. Med, Nov. 2, 1204–1207.
Barba et al (1994) Proced. Natl. Acad Sci. 91, 4348–4352.

*Primary Examiner*—Deborah Crouch
*Attorney, Agent, or Firm*—Townsend and Townsend and Crew LLP

[57] ABSTRACT

In its broadest terms, the invention provides methods for the enhanced intracellular delivery of therapeutically active molecules to a target tumor cell. In a preferred embodiment, the method comprises providing engineered cells that express a heterologous nucleic acid that encodes a connexin and that contain a pro-drug activating gene, and contacting target tumor cells in a solid tumor with engineered cells that form functional gap junctions with said target tumor cells, such that the therapeutic molecule passes through a gap junction to a target tumor cell. More particularly, the invention involves providing engineered non-tumorigenic cells that express a first heterologous nucleic acid that encodes a connexin and a second heterologous nucleic acid that encodes a pro-drug activating molecule that converts a nontoxic substrate to a toxic metabolite, then contacting tumor cells in a solid tumor with engineered cells that form functional gap junctions with said tumor cells, and then exposing the engineered and tumor cells to the nontoxic substrate, whereby the nontoxic substrate is converted to the toxic metabolite in cells that expresses the pro-drug activating molecule, and the toxic metabolite then passes through gap junctions to adjacent coupled tumor cells, thereby inhibiting the cell growth of the tumor cells that contain the toxic metabolite.

11 Claims, 6 Drawing Sheets

(1 of 6 Drawing Sheet(s) Filed in Color)

METHOD FOR INHIBITING TUMOR CELL GROWTH BY ADMINISTERING TO TUMOR CELLS EXPRESSING A NUCLEIC ACID ENCODING A CONNEXIN AND A PRO-DRUG

This application is a continuation-in-part of U.S. provisional application Ser. No. 60/010,930, filed on Jan. 31, 1996.

BACKGROUND OF THE INVENTION

The invention relates to cancer therapies, to gene therapies for treating cancer, and to in vivo methods for transferring molecules from engineered cells into other cells.

A gap junction is a membrane structure detectable at points of contact between adjacent cells. Gap junctions mediate the intercellular passage of small molecules from the cytoplasm of one cell to that of the adjacent cell.

Gap junctions are composed of clusters of membrane proteins which form structures called connexons. The proteins are peripherally disposed around a central channel. Gap junction transmembrane passages are formed when a connexon of one cell aligns with a connexon of an adjacent cell. In this way, transmembrane intercellular pathways are formed that permit the passage of molecules between coupled cells.

The diameter of the connexon channels, as measured by electron microscopy and X-ray crystallography, is about 1.5–2 nm. Based on this measurement, one would expect that only substances of less than approximately 1,000 daltons (ions, small molecules and synthetic oligonucleotides, but not macromolecules such as proteins and polynucleotides) would enter the channel and pass from one cell to another. This prediction has been verified experimentally. Sugars, nucleic acids, amino acids, fatty acids, small peptides, and even drugs or carcinogens could pass between cells through gap junctions. Proteins, complex lipids, polysaccharides, RNA, and other large molecules do not. This intercellular channel flux of ions and molecules does not require energy and is reportedly due to passive diffusion.

The protein subunits of connexons may vary from cell to cell. Some connexons contain ductin. Finbow and Pitts, *J. Cell Sci.* 106: 463–472 (1993); Leitch and Finbow, *Exp. Cell Res.* 190: 218–226 (1990); Bohrmann, *J. Cell Sci.* 105: 513–518 (1993). Some connexons contain connexins. See Beyer et al., *J. Membr. Biol.*, 116:187–194 (1990), and references cited therein.

More than a dozen connexon proteins have been cloned from different species. The best characterized of the connexon proteins, the connexins, are the gene products of a multi-gene family. Connexins are expressed in a cell-, tissue-, and developmentally specific manner. See Beyer et al., *J. Membr. Biol.*, 116:187–194 (1990); Dermietzel, R. et al., *Anat. Embryol.*, 182:517–258 (1990; Warner, A., *Seminars in Cell Biology*, 3:81–91 (1992); Kumar, N. M. et al., *Seminars in Cell Biology*, 3:3–16 (1992). For instance, connexin43 is the predominant connexin expressed in cardiac muscle and in liver epithelial cells. In adult liver parenchymal cells, the predominant connexins are connexins32 and connexin26; nonparenchymal liver cells express other connexins. Each connexin forms channels with different conductance, regulatory, and permeability properties.

In those tissues where more than one connexin is expressed, gap junctions may contain more than one connexin. However, it is not known whether individual connexons may be comprised of more than one connexin type. Individual cells that are coupled by gap junctions to neighboring cells do not always behave as discrete entities. Rather, two or more coupled cells often function in a highly integrated manner. Instead of responding individually to certain environmental stimuli, they respond as a unit. In this way tissues can buffer or eliminate toxic compounds that would otherwise be harmful to individual cells, healthy cells can nourish injured cells, and critical molecules can be distributed among cells to coordinate local functions. For example, it has been proposed that gap junctions play an important role in the function of cardiac muscle cells. The rapid intercellular exchange of ions through gap junctions is believed to mediate coordinated contraction of the myocardium.

Gap junctional communication appears to contribute to what has been variously termed the "kiss of death," the "kiss of life" or the "bystander effect". When cells that are normally insensitive to a given substance are connected via gap junctions to cells that are normally sensitive, the insensitive cells become sensitive ("kiss of death"), reportedly because of the passage of toxic molecules from the sensitive to the insensitive cells. On the other hand, when certain cells that are unable to survive in defined tissue culture media are joined to cells that are capable of surviving, in some instances the sensitive cells acquire the ability to survive, reportedly because of the passage of molecules from survivalist cells to sensitive cells ("kiss of life").

The ability of adjacent cells to form gap junctions that link them is dependent on a number of factors:

a) the ability of cells to interact with neighboring cells. It has been reported that the presence of compatible cell adhesion molecules is an important requirement of gap junctional formation between adjacent cells. See Edelman, G. M., *Biochem*, 27:3533–3543 (1988); Meyer, R. A. et al., *J. Cell Biol.*, 119:179–189 (1992); Keane, R. W. et al., *J. Cell Biol.*, 106:1307–1319 (1988); Musil, L. S. et al., *J. Cell Biol.*, 111:2077–2087 (1990); Jongen et al., *J. Cell Biol.*, 114:545–555 (1991); Hofer et al. *J. Neuroscience* 16(14)4311–21 (1996).

b) it has been reported that increased levels of connexon protein expression results in increased gap junction communication. See Eghabali et al., *Proc. Natl. Acad. Sci. USA*, 87:1328–1331 (1990); Zhu et al., *Proc. Natl. Acad. Sci. USA*, 89:10218–10221 (1992); and Zhu et al., *Proc. Natl. Acad. Sci. USA*, 88:1883–1887 (1991); Mesnil et al. *Proc. Natl. Acad. Sci. USA*, 93(5):1831–5. (1996); Bruzzone et al. *Eur. J. Biochem.* 238(1):1–27 (1996); Shinoura et al., *J. Neurosurg.* 84(5):839–45 (1996); Fishman et al., *Cell Adhesion and Communication* 3(4):353–65 (1995); Elfgang et al. *J. Cell Biol.* 129(3):805–17 (1995); Koval et al., *J. Cell Biol.* 130 (4):987–95 (1995); Moore et al., *Amer. J. Physiol.* 267(5 Pt 1):C1371–80 (1994);

c) whether the connexon proteins expressed by one cell are capable of forming a connexon that is capable of linking with a connexon of a second cell to form a functional channel.

d) whether a molecule such as a carcinogen or the product of an oncogene is expressed in a cell, that interferes with the normal function of any cellular protein that mediates cell to cell gap junctional communication. See Holder et al., *Cancer Research*, 53:3475–3485 (1993).

It has been reported that cancer cells exhibit reductions in gap junction-mediated intercellular communication compared to normal cells with a similar tissue origin. While neoplastic cells can sometimes form gap junctions with other types of cells (heterologous coupling), it is recognized that gap function formation between cells of a similar type (homologous coupling) can be more efficient.

It has been repeatedly observed that coupling normal cells to tumor cells slows down the growth of tumor cells. Also, experimental techniques that result in an increase in gap function channels can reduce cellular proliferation and tumorigenicity.

Since gap junctional communication appears to play a role in neoplasia, it has been suggested that increasing gap junctional communication should reverse neoplasia. Connexin gene expression can be increased in malignant cell lines by the introduction of connexin genes. The proliferation rate of tumor cell growth in tissue culture, as well as tumor formation after injection into animals have been found to be reduced in cells that were genetically engineered to overexpress connexin genes.

A new method for tumor gene therapy uses recombinant retroviral vectors containing a gene (HSVtk) that encodes the thymidine kinase enzyme of the herpes simplex virus (HSVTK). Following infection of a tumor cell by the retroviral vector, the HSVtk gene is expressed therein. The HSVTK enzyme avidly phosphorylates certain nucleoside analogues, such as the drug Ganciclovir (GCV), for which normal mammalian thymidine kinase has a poor affinity. These phosphorylated analogues are incorporated into the cellular genome during DNA replication, leading to tumor cell death. Exposure to GCV does not appear to harm normal cells when given in therapeutic doses.

A recognized limitation of this therapy is the relative inefficiency of gene transfer. Also, retroviral particles are relatively rapidly inactivated by host organism defenses, such as complement. In addition, a target cell must be replicating for the DNA to be stably integrated. Only a minority of tumor cells can be genetically altered after retroviral infection, especially in vivo.

SUMMARY OF THE INVENTION

It is a principal object of the invention to provide methods for treating tumors, especially rapidly growing tumors, in subjects in need thereof. In particular, it is an object of the invention to provide cells that are genetically engineered to increase their ability to interact with and to inhibit tumor cells. Still more particularly, it is an objective to provide genetically engineered cells that synthesize or modify molecules that pass through gap junctions and inhibit the growth of tumor cells.

Accordingly, the present invention provides methods of inhibiting the growth of tumor cells, which methods comprise:

a) providing engineered non-tumorigenic cells that express a first heterologous nucleic acid that encodes a molecule which enables, mediates or enhances the gap junctional transport of therapeutic molecules and a second heterologous nucleic acid which encodes a molecule with desired biological effects capable of passing through a gap junction or a pro-drug activating molecule that converts a non-toxic substrate to a toxic metabolite.

b) contacting tumor cells in a solid tumor with cells of step a that form functional gap junctions with said tumor cells, and then c) in the case of therapeutic strategies utilizing pro-drug activating molecules, exposing the engineered and tumor cells to the non-toxic substrate, whereby the non-toxic substrate is converted to the toxic metabolite in cells that expresses the pro-drug activating molecule, and the toxic metabolite then passes through gap junctions to adjacent coupled tumor cells, thereby inhibiting the cell growth of the tumor cells that contain the toxic metabolite.

The engineered cells may be derived from neoplastic and nonneoplastic established cell lines, cells from primary cultures established from tumor specimens, cultured cells from serial passages of surgical tumor specimens, and cultured cells isolated from normal tissues. Cell types include, but are not limited to, fibroblast, endothelial, smooth and skeletal muscle, parenchymal, hematopoietic, lymphoid, epithelial, neuroectodermal, mesodermal, mesenchymal, bone or keratinocyte cell lines. These cells include, but are not limited to, rodent, feline, canine, bovine, equine, ovine, nonhuman primate, or human origin. A particular example are murine PA317 fibroblasts. The tumors to be treated include all types of neoplastic cells. The pro-drug system involves, for example, thymidine kinase, cytosine deaminase, or $\beta$-glucosidase. Molecules that enable, mediate or enhance gap junctional transport include, but are not limited to, cadherins; connexins; catenins; caveolin, ductin; desmocollin; desmoglein; desmoplakin; plakoglobin; cytoskeleton proteins such as ankyrin, ezrin, fodrin, moesin, paxilin, radixin, talin, tensin, and vinculin; APC protein; DCC protein; Wnt proteins; integrins; and tight junction proteins such as ZO-1 and occludin.

The present invention further comprises methods for the enhanced intracellular delivery of one or more therapeutically active molecules to target tumor cells, which method comprises:

a) providing engineered cells that contain or can generate a therapeutically active molecule that passes through gap junctional channels, wherein the engineered cells express a heterologous nucleic acid that encodes a molecule that enables or enhances the extent of gap junction mediated intercellular communication. Such molecules include but are not limited to cellular adhesion molecules or connexon proteins that are expressed by the tumor cells described in step b, and b) contacting target tumor cells in a solid tumor with cells of step a that form functional gap junctions with said target tumor cells, whereby the molecule passes through a gap junction to a target tumor cell.

The invention further comprises compositions for the enhanced delivery of toxic metabolites to target tumor cells, which compositions comprise engineered cells that express a first heterologous nucleic acid that encodes a connexon protein and a second heterologous nucleic acid that encodes a therapeutic small molecule or a pro-drug activating molecule, and optionally a molecule other than a connexon protein that enables, mediates or enhances gap junctional intercellular communication. The tumor cells may be glioma cells, colon carcinoma cells, prostate cancer cells, breast cancer cells, lung cancer cells, kidney cancer cells, kidney cancer cells, osteosarcoma cells, and neuroblastoma cells.

The file of this patent contains at least one drawing executed in color. Copies of this patent with color drawings will be provided by the Patent and Trademark Office upon request and payment of the necessary fee.

DETAILED DESCRIPTION OF THE INVENTION

Figure 1:
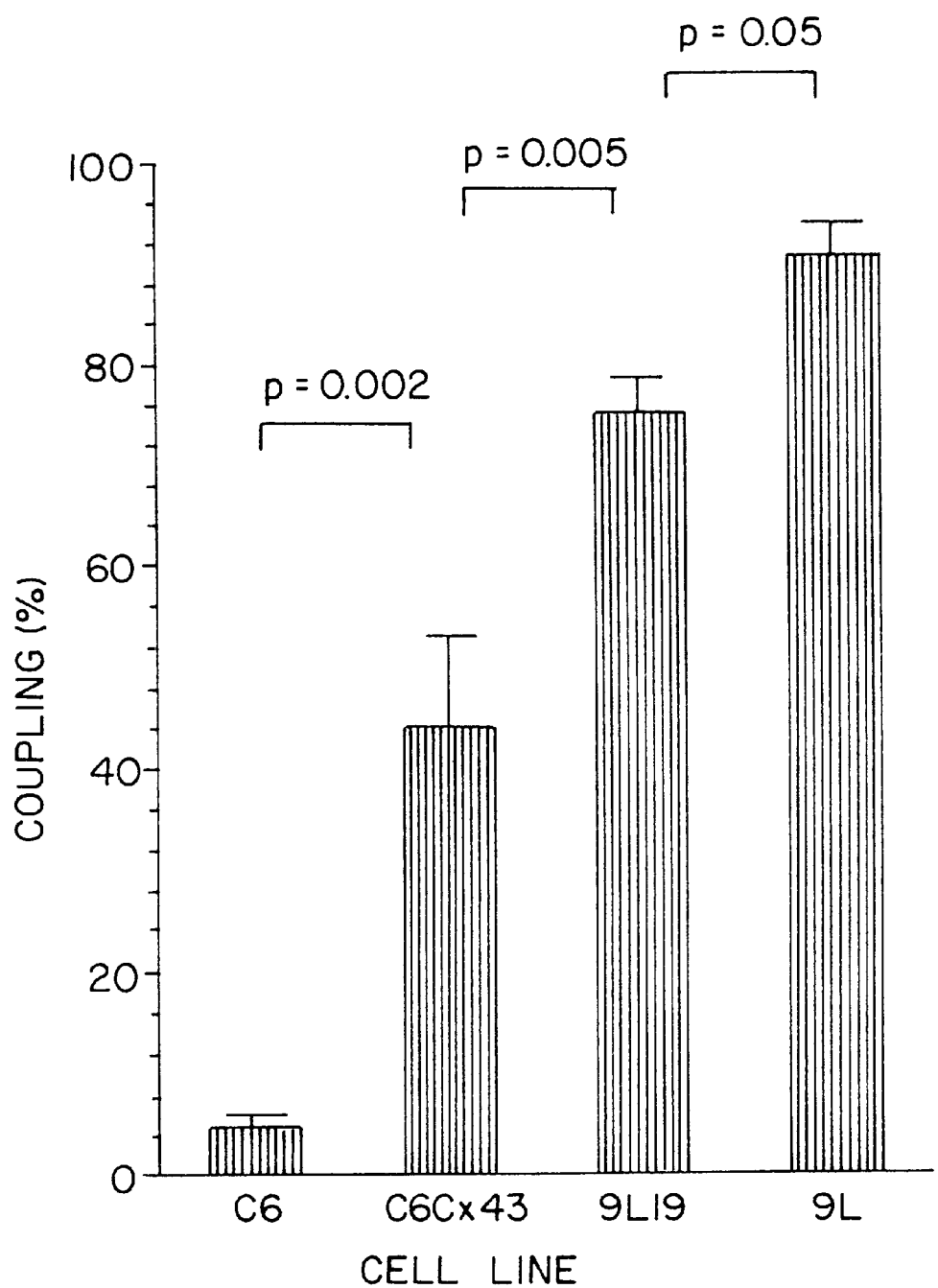
FIG. 1 depicts the coupling achieved between cells in tissue culture.

The patents and publications cited in this disclosure reflect the level of skill in the art to which this invention pertains and are herein individually incorporated by reference for all puposes.

Unless defined otherwise, all technical and scientific terms used herein have the same meaning as commonly understood by one of ordinary skill in the art to which this invention belongs. Singleton et al., *Dictionary of Microbiology and Molecular Biology*, second edition, John Wiley and Sons (New York) (1994), provides one of skill with a general dictionary of many of the terms used in this invention. Although any methods and materials similar or equivalent to those described herein can be used in the practice or testing of the present invention, the preferred methods and materials are described. For purposes of the present invention, the following terms are defined below.

A. Definitions

The term "tumor cell" or "cancer cell" or "neoplastic cell" denotes a cell that demonstrates inappropriate, unregulated proliferation. A "human" tumor is comprised of cells that have human chromosomes. Such tumors include those in a human patient, and tumors resulting from the introduction into a nonhuman host animal of a malignant cell line having human chromosomes into a nonhuman host animal.

"Non-tumorigenic cell" is a cell that is unable to form a tumor when introduced into a host organism. Examples include fibroblasts, epithelial cells, endothelial cells, bone cells, keratinocytes, and any cell that can be cultured in tissue culture, including tissue explants. Another kind of non-tumorienic cells are cells that are normally tumorigenic but are treated to remove their tumorigenicity, for example, irradiated, engineered non-tumorigenic cells derived from tumors.

The phrase "inhibiting cell growth" or "inhibiting tumor growth" generally means that the rate of increase in mass, size, number and/or the metabolism of treated cells and/or tumors is slower as a result of treatment than that of nontreated cells and/or tumors. The growth of a cell line or tumor is said to be "inhibited" by a treatment if, when assayed by means such as radioisotope incorporation into the cells, the treated cells increase in number at a rate that is less than the proliferation rate of untreated control cells, and preferably less than about 50% of the untreated cell proliferation rate. More preferably, the growth rate is inhibited by at least 80%. If growth is assayed by a means such as plating in methylcellulose, the growth of a cell line is said to be "inhibited" if the treated cells give rise to less than the number of colonies that grow from a like number of untreated cells. Preferably, the number of colonies from treated cells is less than about 70% of the number from untreated cells. More preferably, the number of colonies is decreased by at least 50%. "Inhibition of cell growth" also encompasses zero growth and, most importantly, consequent death of the tumor cells and eradication of the tumor. When measured in vivo, "inhibition of tumor growth" encompasses fewer or smaller tumors (for example, smaller diameter) as compared to control animals or untreated patients.

Inhibition can be evaluated by any accepted method of measuring whether growth or size of the tumor and/or increase in the number of cancerous or tumor cells has been slowed, stopped, or reversed. This includes direct observation and indirect evaluation such as subjective symptoms or objective signs. The clinician may notice a decrease in tumor size or tumor burden (number of tumors) based on physical exam, laboratory parameters, tumor markers, or radiographic findings. Alternatively, if the mammal is human, the patient may note improved vigor or vitality or decreased pain as subjective symptoms of improvement or response to therapy. Some laboratory signs that the clinician may observe for response to therapy include normalization of tests such as white blood cell count, red blood cell count, platelet count, erythrocyte sedimentation rate, and various enzyme levels such as transaminases and hydrogenases. Additionally, the clinician may observe a decrease in a detectable tumor marker such as prostatic specific antigen (PSA) or chorio embryonic antigen (CEA). Alternatively, other tests can be used to evaluate objective improvement such as monograms, computerized axial tomography scans, nuclear magnetic resonance scans and positron emission testing.

The term "nucleic acid" refers to deoxyribonucleotides or ribonucleotides, and polymers thereof in either single- or double-stranded form, and unless specifically limited, encompasses known analogues of natural nucleotides. Unless otherwise indicated, a particular nucleic acid sequence implicitly encompasses conservatively modified variants thereof and complementary sequences and as well as the sequence explicitly indicated.

The phrase "heterologous nucleic acid" generally denotes a nucleic acid that has been isolated, cloned and introduced into and/or expressed in a manner, cell or cellular environment other than the manner, cell or cellular environment in which said nucleic acid or protein may typically be found in nature. The term encompasses both nucleic acids originally obtained from a different organism or cell type than the cell type in which it is expressed, and also nucleic acids that are obtained from the same cell line as the cell line in which it is expressed.

The phrase "a nucleic acid sequence encoding" refers to a nucleic acid which contains sequence information that, if translated, yields the primary amino acid sequence of a specific protein or peptide. This phrase specifically encompasses degenerate codons (i.e., different codons which encode a single amino acid) of the native sequence or sequences which may be introduced to conform with codon preference in a specific host cell.

The term "recombinant" or "engineered" when used with reference to a cell indicates that the cell replicates or expresses a nucleic acid or expresses a peptide or protein encoded by a nucleic acid, whose origin is exogenous to the cell. Recombinant cells can express nucleic acids that are not found within the native (nonrecombinant) form of the cell. Recombinant cells can also express nucleic acids natively expressed in the cell, wherein the nucleic acids are reintroduced into the cell by artificial means in order to alter the expression of that gene.

The phrase "cellular adhesion molecules" denotes molecules or complexes of molecules present at the external surfaces of cells that mediate the contact and/or recognition and/or adhesion of adjoining cells. Pouliot et al., *BioEssays* 14:743–748 (1992). Molecules which enable, mediate or enhance gap junction mediated intercellular communication include, but are not limited to, cadherins (Walsh, F. S. et al., *J. Neurochem.*, 55:805–812 (1990); Bussemakers, M. J. et al., *Mol. Biol. Rep.*, 17:123–128 (1993); Grumet, M. et al., *J. Cell Biol.*, 113:1399–1412 (1991); Shimoyama, Y. et al., *J. Cell Biol.*, 109:1787–1794 (1989); Suzuki, S. et al., *Cell Regul.*, 2:261–270 (1991); Tanihara, H. et al., *Cell Adhesion Commun.*, 2:15–26 (1994); Tanihara, H. et al., *Cell Adhesion Commun.*, 2:15–26 (1994); Okazaki et al. *J. Biol. Chem.* 269 (16): 12092–8 (1994) Breviario, F. et al., *Arterioscler. Thromb. Vasc. Biol.*, 15:1229–1239 (1995); and Selig, S. et al., *Proc. Natl. Acad. Sci. USA,* 92:3702–3706 (1995)); connexins (Fishman, G. I. et al., *Genomics,* 10:250–256 (1991); Lee, S. W. et al., *J. Cell Biol.*, 118:1213–1221 (1992); Reed, K. E. et al., *J. Clin. Invest.*; Dahl et al., *J. Biol. Chem.* 271: 17903–10 (1996 ); 91:997–1004 (1993); Willecke, K. et al., *Eur. J. Cell Biol.*, 58:81–89 (1992); Paul, D. L. et al., *J. Cell Biol.*, 115:1077–1089 (1991); Haefliger, J. A. et al., *J. Biol. Chem.*, 267:2057–2064 (1992);; Willecke, K. et al., *Eur. J. Cell Biol.*, 56:1–7 (1991); Haefliger, J. A. et al., *J. Biol. Chem.* 267: 2057–64 (1992); and Tucker, M. A. et al., *Exp. Cell Res.*, 213:224–230 (1994)); catenins (Hulsken, J. et al., *J. Cell Biol.*, 127:2061–2069 (1994); Rimm, D. et al., *Biochem. Biophys. Res. Commun.*, 203:1691–1699 (1994); Rimm, D. L. et al., "Molecular Cloning Reveals Alternative Splice Forms of Human alpha(E)-catenin," unpublished (1993); Lo et al. *J. Biol. Chem.* 269 (35): 22310–9 (1994); and Furukawa, Y. et al., *Cytogenet. Cell Genet.*, 65:74–78 (1994)); ductin (Finbow, M. E. et al., *J. Cell Sci.*, 107:1817–1824 (1994)); desmocollin (Parker, A. E. et al., *J. Biol. Chem.*, 266:10438–10445 (1991)); desmoglein (Buxton, R. S. (1990); Schaefer, S. et al., "Cytoskeletal Architecture and Epithelial Differentiation: Molecular Determinations of Cell Interactions Cytoskeletal Filament Anchorage," unpublished; Zimbelmann, R. (1993); and Schafer, S. et al., *Exp. Cell Res.*, 211:391–399 (1994)); desmoplakin (Virata, M. L. et al., *Proc. Natl. Acad. Sci. USA,* 89:544–548 (1992)); plakoglobin (Franke, W. W. et al., *Proc. Natl. Acad. Sci. USA,* 86:4027–4031 (1989)); cytoskeleton proteins such as ankyrin (Lux, S. E. et al., *Nature,* 344:36–42 (1990); Otto, E. et al., *J. Cell Biol.*, 114:241–253 (1991); and Lamert, S. et al., *Proc. Natl. Acad. Sci. USA,* 87:1730–1734 (1990)), ezrin (Hunter, T. (1990); and Gould, K. L. et al., *Embo. J.*, 8:4133–4142 (1989)), fodrin, moesin (Lankes, W. T. et al., *Proc. Natl. Acad. Sci. USA* (in press) (1991)), paxilin, radixin (Wilgenbus, K. K. et al., *Genomics,* 16:199–206 (1993)), talin (Rees, D. J. et al., *Nature,* 347:685–689 (1990); and Liew, C. C. et al., *Proc. Natl. Acad. Sci. USA,* 91:10645–10649 (1994)), tensin (Chen, L. B., "Full Length Nucleotide Sequence of Tensin from a Chicken Embryo Fibroblast cDNA Library," unpublished (1992); Davis et al., *Science* 252 (5006): 712–5 (1991); and Liew, C. C. et al., *Proc. Natl. Acad. Sci. USA,* 91:10645–10649 (1994)), and vinculin (Weller, P. A. et al., *Proc. Natl. Acad. Sci. USA,* 87:5667–5671 (1990)); APC protein (Kinzler, K. W. et al., *Science,* 253:661–665 (1991)); DCC protein (Cooper, H. M. et al., unpublished (1995); Hedrick, L. et al., *Genes Dev.*, 8:1174–1183 (1994); and Cho, K. R. et al., *Genomics,* 19:525–531 (1994)); Wnt proteins (Gavin, B. J. et al., *Genes Dev.*, 4:2319–2332 (1990)); integrins (Takada, Y. et al., *J. Cell Biol.*, 109:397–407 (1989); and Takada, Y. et al., *Embo. J.*, 8:1361–1368 (1989)); and tight junction proteins such as ZO-1 and occludin (Willott, E. et al., *Am. J. Physiol.*, 262:1119–1124 (1992); Willott, E. et al., *Proc. Natl. Acad. Sci. USA,* 90:7834–8 (1993); and Furuse, M. et al., *J. Cell Biol.*, 123:1777–1788 (1993)). The connexin is, for example, connexin 26, 32, 43, or 45. The sequences of these proteins have been published, and many are available from the American Type Tissue Collection or from commercial sources. The engineered cells and the target cells may be obtained or derived from the same individual, different individuals, or different species.

The term "connexon protein" denotes a protein that forms part of the physical structure of a connexon. Examples include connexins and ductins.

The term "connexin" denotes a family of genes and gene products wherein the gene products are structural subunits of gap junctions, and variants thereof. "Connexin" further denotes nucleic acid sequences and their gene products, wherein the gene products are recognized by antibodies that specifically bind to a connexin protein and, when expressed in cells, may be present in gap junctions. For a discussion of the connexin family of proteins, see Beyer et al., *J. Membr. Biol.*, 116:187–194 (1990), and references cited therein.

"Ductin" refers to gap junctional components described in Finbow and Pitts (1993), *J. Cell Sci.* 106: 463–472; Leitch and Finbow (1990), *Exp. Cell Res.* 190: 218–226; Bohrmann (1993), *J. Cell Sci.* 105: 513–518. Ductin further denotes nucleic acid sequences and their gene products which, when expressed in cells, may be present in gap junctions, and wherein the gene products are recognized by antibodies that specifically bind to a ductin protein.

"Coupled cells" or "gap junctional partners" denotes adjacent cells whose cytoplasmic domains are connected by gap junctions. That is, molecules may pass from one cell to the other via the gap junctions.

The term "pro-drug" refers to substances that are themselves not substantially toxic at therapeutic doses, but that become very toxic, either when chemically altered or metabolized by cells capable of altering or metabolizing the pro-drug, or when combined with other substances to form a complex that is toxic. Examples include 5-fluorocytosine ("5FC"), which can be converted to the lethal metabolite 5-fluorouracil ("5FU"); 5-methoxypurine arabinoside; and ganciclovir (GCV). A "therapeutic dose" or therapeutic amount of a pro-drug is a dose that causes no substantial ill effects to an organism except to cells that are capable of converting the pro-drug to a toxic product (i.e., metabolite or complex). "Pro-drug activating molecule" refers to a molecule such as an enzyme that is capable of metabolizing the non-toxic pro-drug to its toxic metabolite, or a molecule that combines (covalently or non-covalently) with a pro-drug to yield a toxic product.

The phrase "expresses a pro-drug sensitivity" signifies that a cell is rendered susceptible to a pro-drug by virtue of expressing a gene product that is capable of converting a nontoxic pro-drug into a cytotoxic chemical substance or complex. For example, the enzyme cytosine deaminase converts 5-fluorocytosine ("5FC") into the lethal metabolite 5-fluorouracil ("5FU"). Host cells that are induced to produce cytosine deaminase by virtue of having the cytosine deaminase gene introduced into and expressed in the host cell, when exposed to 5FC, will die as a result of the formation of 5FU. Another gene that confers drug sensitivity upon a host cell is the thymidine kinase gene, which confers sensitivity to GCV. See Ido et al., *Cancer Research,* 55:3105 (1995); Izquierdo et al., *Gene Therapy,* 2:66 (1995). Other such "drug sensitivity" or "suicide" genes are known in the art, and are expressly encompassed by the present invention.

It should be noted that treatments such as GCV treatment are most effective in cells that are undergoing cell division. Thus, terminally differentiated non-dividing cells such as most neurons do not exhibit marked growth inhibition upon treatment. Dividing tumor cells that are exposed to the activated pro-drug, on the other hand, should have their growth inhibited.

The phrase "heterologous nucleic acid that encodes a molecule that enables, mediates or enhances gap junctional communication" in the context of the claims includes, but is not limited to, nucleic acids encoding cadherins; catenins; desmocollin; desmoglein; desmoplakin; plakoglobin; cytoskeleton proteins such as ankyrin, ezrin, fodrin, moesin, paxilin, radixin, talin, tensin, and vinculin; APC protein; DCC protein; Wnt proteins; integrins; and tight junction proteins such as ZO-1 and occludin.

The phrase "a therapeutically active molecule" means a molecule that can pass from one junctional partner to another through gap junctional channels and that alters the chemistry, growth, or metabolism of the cell into which it passes.

The phrase "effective amount" means a dosage sufficient to produce a desired result. The desired result can be subjective or objective improvement in the recipient of the dosage, a decrease in tumor size, a decrease in the rate of growth of cancer cells, a decrease in metastasis, or any combination of the above.

B. General methods for introduction of connexon protein or selected genes into cells An important aspect of this invention are methods for introducing connexon proteins and/or selected genes (e.g., pro-drug sensitivity genes) into cells. Standard eukaryotic transduction methods are used to produce cell lines which express connexon protein and, optionally, a drug resistance gene. It is expected that those of skill in the art are knowledgeable in the numerous systems available for transferring, cloning and expressing nucleic acids.

In brief summary, the expression of natural or synthetic nucleic acids is typically achieved by operably linking a nucleic acid of interest (e.g., one encoding connexin) to a promoter (which is either constitutive or inducible) and incorporating the construct into an expression vector. The vectors are suitable for replication and/or expression in prokaryotes, eukaryotes, or preferably both. Typical cloning vectors contain transcription and translation terminators, transcription and translation initiation sequences, and promoters useful for regulation of the expression of the particular nucleic acid. The vectors optionally comprise expression cassettes containing at least one independent terminator sequence, sequences permitting replication of the cassette in eukaryotes, or prokaryotes, or both, (e.g., shuttle vectors) and selection markers for both prokaryotic and eukaryotic systems. See Giliman and Smith, *Gene*, 8:81–97 (1979); Roberts et al., *Nature*, 328:731–734 (1987); Berger and Kimmel, *Guide to Molecular Cloning Techniques, Methods in Enzymology*, volume 152, Academic Press, Inc., San Diego, Calif. (Berger); Sambrook et al., *Molecular Cloning—A Laboratory Manual* (2nd ed.) Vol. 1–3, Cold Spring Harbor Laboratory, Cold Spring Harbor Press, N.Y. (1989), (Sambrook); and Ausubel, F. M. et al., *Current Protocols in Molecular Biology*, eds., Current Protocols, a joint venture between Greene Publishing Associates, Inc. and John Wiley & Sons, Inc., (1994 Supplement) (Ausubel). Product information from manufacturers of biological reagents and experimental equipment also provide information useful in known biological methods. Such manufacturers include the SIGMA chemical company (Saint Louis, MO), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), and Applied Biosystems (Foster City, Calif.), as well as many other commercial sources known to one of skill.

The expression vector typically comprises a prokaryotic replicon covalently linked to an eukaryotic transcription unit or expression cassette that contains all the elements required for the expression of exogenous connexon protein in eukaryotic cells. A typical expression cassette contains a promoter linked to the DNA sequence encoding the selected connexon protein and signals required for efficient polyadenylation of the transcript.

Eukaryotic promoters typically contain at least two types of regulatory sequences, the TATA box and upstream promoter elements. The TATA box, located 25–30 base pairs upstream of the transcription initiation site, is thought to be involved in directing RNA polymerase to begin RNA synthesis. The other upstream promoter elements may determine the rate at which transcription is initiated.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus, the long term repeat from various retroviruses such as murine leukemia virus, murine or Rous sarcoma virus and HIV. See *Enhancers and Eukaryotic Expression*, Cold Spring Harbor Press, Cold Spring Harbor, N.Y. (1983), which is incorporated herein by reference.

In the construction of the expression cassette, the promoter is preferably positioned about the same distance from the heterologous transcription start site as it is from the transcription start site in its natural setting. As is known in the art, however, some variation in this distance can be accommodated without loss of promoter function.

In addition to a promoter sequence, the expression cassette should also contain a transcription termination region downstream of the connexon protein structural gene to provide for efficient termination. The termination region may be obtained from the same source as the promoter sequence or may be obtained from a different source.

If the mRNA encoded by the connexon protein structural gene is to be efficiently translated, polyadenylation sequences are also commonly added to the vector construct. Two distinct sequence elements are required for accurate and efficient polyadenylation: GU or U rich sequences located downstream from the polyadenylation site and a highly conserved sequence of six nucleotides, AAUAAA, located 11–30 nucleotides upstream. Termination and polyadenylation signals that are suitable for the present invention include those derived from SV40, or a partial genomic copy of a gene already resident on the expression vector.

In addition to the elements already described, the expression vector of the present invention may typically contain other specialized elements intended to increase the level of expression of cloned nucleic acids or to facilitate the identification of cells that carry the transduced DNA. For instance, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not comprise a eukaryotic replicon. If a eukaryotic replicon is present, then the vector may be amplifiable in eukaryotic cells using the appropriate selectable marker. If the vector does not comprise a eukaryotic replicon, no episomal amplification is possible. Instead, the transduced DNA integrates into the genome of the engineered cell, where the promoter directs expression of the desired nucleic acid.

The vectors may include selectable markers which can be used for nucleic acid amplification such as the sodium, potassium ATPase, thymidine kinase, aminoglycoside phosphotransferase, hygromycin B phosphotransferase, xanthine-guanine phosphoribosyl transferase, CAD (carbamyl phosphate synthetase, aspartate transcarbamylase, and dihydroorotase), adenosine deaminase, dihydrofolate reductase, and asparagine synthetase and ouabain selection. Alternatively, high yield expression systems not involving nucleic acid amplification are also suitable, such as using a bacculovirus vector in insect cells, with connexon protein encoding sequence under the direction of the polyhedrin promoter or other strong baculovirus promoters.

The expression vectors of the present invention will typically contain both prokaryotic sequences that facilitate the cloning of the vector in bacteria as well as one or more eukaryotic transcription units that are expressed only in eukaryotic cells, such as mammalian cells. The prokaryotic sequences are preferably chosen such that they do not interfere with the replication of the DNA in eukaryotic cells.

Once a nucleic acid is synthesized or isolated and inserted into a vector and cloned, one may express the nucleic acid in a variety of recombinantly engineered cells known to those of skill in the art. Expression of a an exogenous nucleic acid can be enhanced by including multiple copies of, for example, a connexon protein-encoding nucleic acid in an engineered cell, by selecting a vector known to reproduce in the host, thereby producing large quantities of protein from exogenous inserted DNA (such as pUC8, ptac12, or pIN-III-ompA1, 2, or 3), or by any other known means of enhancing peptide expression. Connexon protein molecules will be expressed when the DNA sequence is functionally inserted into a vector. "Functionally inserted" means that it is inserted in proper reading frame and orientation and operably linked to proper regulatory elements. Typically, a connexon protein gene will be inserted downstream from a promoter and will be followed by a stop codon. However, production as a hybrid protein optionally followed by cleavage may be used, if desired.

1. Vectors for introduction and expression of connexon protein in cells

Vectors to which connexon protein-encoding nucleic acids are operably linked may be used to introduce these nucleic acids into host cells and mediate their replication and/or expression. "Cloning vectors" are useful for replicating and amplifying the foreign nucleic acids and obtaining clones of specific foreign nucleic acid-containing vectors. "Expression vectors" mediate the expression of the foreign nucleic acid. Some vectors are both cloning and expression vectors.

In general, the particular eukaryotic expression vector used to transport connexon protein or any other gene into the cell may not be particularly critical. Any of the conventional vectors used for expression in eukaryotic cells may be used. Expression vectors containing regulatory elements from eukaryotic viruses such as retroviruses are typically used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A$^+$, pMTO10/A$^{30}$, pMAMneo-5, baculovirus pDSVE, and any other vector allowing expression of proteins under the direction of promoters derived from the SV-40 early promoter, SV-40 later promoter, metallothionein promoter, murine mammary tumor virus promoter, Rous sarcoma virus promoter, polyhedrin promoter, cytomegalovirus promoter, or other promoters shown effective for expression in eukaryotic cells.

While a variety of vectors may be used, it should be noted that retroviral vectors are widely used for modifying eukaryotic cells in vitro because of the high efficiency with which the retroviral vectors transfect target cells and integrate into the target cell genome. Additionally, retroviral vectors are capable of infecting cells from a wide variety of tissues.

Retroviral vectors are produced by genetically manipulating retroviruses. Retroviruses are RNA viruses because the viral genome is RNA. Upon infection, this genomic RNA is reverse transcribed into a DNA copy which is integrated into the chromosomal DNA of transfected cells with a high degree of stability and efficiency. The integrated DNA copy is referred to as a provirus and is inherited by daughter cells as is any other gene. The wild type retroviral genome and the proviral DNA have three genes: the gag, the pol and the env genes, which are flanked by two long terminal repeat (LTR) sequences. The gag gene encodes the internal structural (nucleocapsid) proteins; the pol gene encodes the RNA directed DNA polymerase (reverse transcriptase); and the env gene encodes viral envelope glycoproteins. The 5' and 3' LTRs serve to promote transcription and polyadenylation of virion RNAs. Adjacent to the 5' LTR are sequences necessary for reverse transcription of the genome (the tRNA primer binding site) and for efficient encapsulation of viral RNA into particles (the Psi site). See Mulligan, R. C., In: *Experimental Manipulation of Gene Expression,* M. Inouye (ed), 155–173 (1983); Mann, R. et al. (1983), *Cell,* 33:153–159; Cone, R. D. and Mulligan, R. C., *Proceedings of the National Academy of Sciences, U.S.A.,* 81:6349–6353 (1984).

The design of retroviral vectors is well known to one of skill in the art. See Singer, M. and Berg, P., supra. In brief, if the sequences necessary for encapsidation (or packaging of retroviral RNA into infectious virions) are missing from the viral genome, the result is a cis-acting defect which prevents encapsidation of genomic RNA. However, the resulting mutant is still capable of directing the synthesis of all virion proteins. Retroviral genomes from which these sequences have been deleted, as well as cell lines containing the mutant genome stably integrated into the chromosome are well known in the art and are used to construct retroviral vectors. Preparation of retroviral vectors and their uses are described in many publications including European Patent Application EPA 0 178 220, U.S. Pat. No. 4,405,712, Gilboa, *Biotechniques,* 4:504–512 (1986), Mann et al., *Cell,* 33:153–159 (1983), Cone and Mulligan, *Proc. Natl. Acad. Sci. USA,* 81:6349–6353 (1984), Eglitis, M. A. et al., *Biotechniques,* 6:608–614 (1988), Miller, A. D. et al., *Biotechniques,* 7:981–990 (1989), Miller, A. D., (1992), *Nature,* supra (1992), Mulligan, R. C., supra (1993), and Gould, B. et al., and International Patent Application No. WO 92/07943 entitled "Retroviral Vectors Useful in Gene Therapy." The teachings of these patents and publications are incorporated herein by reference.

Recombinant retroviral vectors useful in the present invention are prepared by inserting a nucleic acid encoding a connexon protein and optionally a drug sensitivity gene into a retrovirus vector and packaging the vector with retroviral capsid proteins by use of a packaging cell line. A packaging cell line is a genetically constructed mammalian tissue culture cell line that produces the necessary viral structural proteins required for packaging, but which itself is incapable of producing infectious virions. On the other hand, retroviral vectors used in conjunction with packaging cell lines lack sequences that encode viral structural proteins but retain the nucleic acid sequences necessary for packaging. To prepare a packaging cell line, an infectious clone of a desired retrovirus, in which the packaging site has been deleted, is constructed. Cells comprising this construct will express all structural proteins but the introduced DNA will be incapable of being packaged. Alternatively, packaging cell lines can be produced by transducing a cell line with one or more expression plasmids encoding the appropriate core and envelope proteins. In these cells, the gag, pol, and env genes can be derived from the same or different retroviruses.

A number of packaging cell lines suitable for the present invention are available in the prior art. Examples of these cell lines include Crip, GPE86, PA317 and PG13. See Miller et al., *J. Virol.,* 65:2220–2224 (1991), which is incorporated herein by reference. Examples of other packaging cell lines are described in Cone, R. and Mulligan, R. C., *Proceedings of the National Academy of Sciences, U.S.A.,* 81:6349–6353 (1984), and in Danos, O. and Mulligan, R. C., *Proceedings of the National Academy of Sciences, U.S.A.,* 85:6460–6464 (1988), Eglitis, M. A et al., *Biotechniques,* 6:608–614 (1988), Miller, A. D. et al., *Biotechniques,* 7:981–990 (1989), also all incorporated herein by reference. Amphotropic or xenotropic envelope proteins, such as those produced by PA317 and GPX packaging cell lines may also be used to package the retroviral vectors.

The resultant retroviral vector particle is generally incapable of replication in the host cell but is capable of integrating into the host cell genome as a proviral sequence containing the selected nucleic acid. As a result, engineered cells that contain the integrated recombinant vector are capable of producing the selected connexon protein and the gene product of the drug sensitivity gene.

In addition to the retroviral vectors mentioned above, cells may be infected or transfected with other eukaryotic vectors, including viral vectors such as adenoviral or adeno-associated viral vectors. See, e.g., *Methods in Enzymology,* Vol. 185, Academic Press, Inc., San Diego, Calif. (D. V. Goeddel, ed.) (1990) or M. Krieger (1990), *Gene Transfer and Expression—A Laboratory Manual,* Stockton Press, New York, N.Y., and the references cited therein. Adeno associated viruses (AAVs) require helper viruses such as adenovirus or herpes virus to achieve productive infection. In the absence of helper virus functions, AAV integrates (site-specifically) into a host cell's genome, but the integrated AAV genome has no pathogenic effect. The integration step allows the AAV genome to remain genetically intact until the host is exposed to the appropriate environmental conditions (e.g., a lytic helper virus), whereupon it re-enters the lytic life-cycle. Other AAV vectors may not integrate. Samulski, *Current Opinion in Genetic and Development,* 3:74–80 (1993), and the references cited therein provides an overview of the AAV life cycle. See also West et al., *Virology,* 160:38–47 (1987); Carter et al., U.S. Pat. No. 4,797,368 (1989); Carter et al., WO 93/24641 (1993); Kotin, *Human Gene Therapy,* 5:793–801 (1994); Muzyczka, *J. Clin. Invest.,* 94:1351 (1994), and Samulski, supra, for an overview of AAV vectors.

Plasmids designed for producing recombinant vaccinia, such as pGS62, (Langford, C. L. et al., *Mol. Cell. Biol.,* 6:3191–3199 (1986)) may also be used. This plasmid consists of a cloning site for insertion of foreign nucleic acids, the P7.5 promoter of vaccinia to direct synthesis of the inserted nucleic acid, and the vaccinia tk gene flanking both ends of the foreign nucleic acid.

2. Cells for expression of connexon protein and cancer therapy

A number of cell types are useful for the practice of this invention and are readily available. These include mammalian non-tumor forming fibroblasts, endothelial cells, smooth muscle cells, parenchymal cells, hematopoietic cells, and lymphoid cells, epithelial cells, bone cells, and keratinocytes. They also include tumor-forming cells which are rendered incapable of forming tumors (for example, by irradiation). These cells may be of rodent, feline, canine, bovine, equine, ovine, nonhuman primate, or human origin. The cells may be primary isolates, immortalized, or genetically modified using techniques known to those of skill in the art.

Specific examples of cell lines useful in the invention are: cell lines which already carry an introduced herpes simplex virus thymidine kinase gene such as PA317, other rodent fibroblast lines which do not carry the HSV-tk gene such as Rat-1, rodent and human tumor cells of different origins with and without the HSV-tk gene such as U87-HSVTK (glioma cells with TK) or SK-MEL-1 (melanoma cells without TK) or cells of special tissue origin such as endothelial cells, HUV-EC-C or lymphocytes such as 5G2.

The culture of cells is well known in the art. Freshney, (*Culture of Animal Cells, a Manual of Basic Technique,* third edition, Wiley-Liss, New York (1994)), Kuchler et al., *Biochemical Methods in Cell Culture and Virology* (1977), Kuchler, R. J., Dowden, Hutchinson and Ross, Inc., and the references cited therein provides a general guide to the culture of cells. Cultured cell systems often will be in the form of monolayers of cells, although cell suspensions are also used.

Other cells used in the methods of the present invention can optionally be immortalized by a variety of techniques known in the art, which include transformation with Epstein-Barr virus or with retroviruses, or the transfection of oncogenes. For example, immortalization by Epstein-Barr virus may be employed, as described in U.S. Pat. No. 4,464,465, incorporated herein by reference. Epstein-Barr virus mutants which lack OriP and OriLyt origins of replication are particularly useful. Other useful method of immortalization are over-expression of a cellular gene for growth control such as c-myc as described by Bartlett et al. (1988), *Proc. Natl. Acad. Sci. USA,* 85: 3255–3259, or using the Rous sarcoma virus long terminal repeat-containing constructs, as described in U.S. Pat. No. 5,443,954, both incorporated herein by reference.

The above-mentioned cell lines may be genetically engineered to express genes that increase the survival of cells in vivo, such as immortalizing genes of viral origin (e.g., E7 and E1A), proto-oncogenes (e.g., c-myc and H-ras), and oncogenes (e.g., mutated ras), tumor suppressor inactivators (e.g., p16, p21), and apoptosis inactivators (e.g., bcl-2). They may also be genetically modified to express genes that stimulate the delivery cells in vivo, e.g., growth factors and growth factor receptors such as alpha or beta fibroblast growth factor, alpha or beta fibroblast growth factor receptor, vascular endothelial growth factor, vascular endothelial growth factor receptor, epidermal growth factor, epidermal growth factor recaptor, platelet-derived growth factor, platelet-derived growth factor receptor, insulin growth factors 1 or 2.

An important element in the transduction experiments is how to decide which cells, vectors and nucleic acids to use. This is generally determined by the identity of the cancer or cancerous tumor to be treated. The cell type and nucleic acids should be chosen to enhance compatibility with the target cancer cell. It is important to first determine which connexon proteins and cell adhesion molecules are expressed in the target cells, and also their tissue origin. The engineered cells used to treat a particular tumor should preferably contain adhesion molecules and connexon proteins that are compatible, and preferably should be derived from a same or similar tissue.

Figure 2:
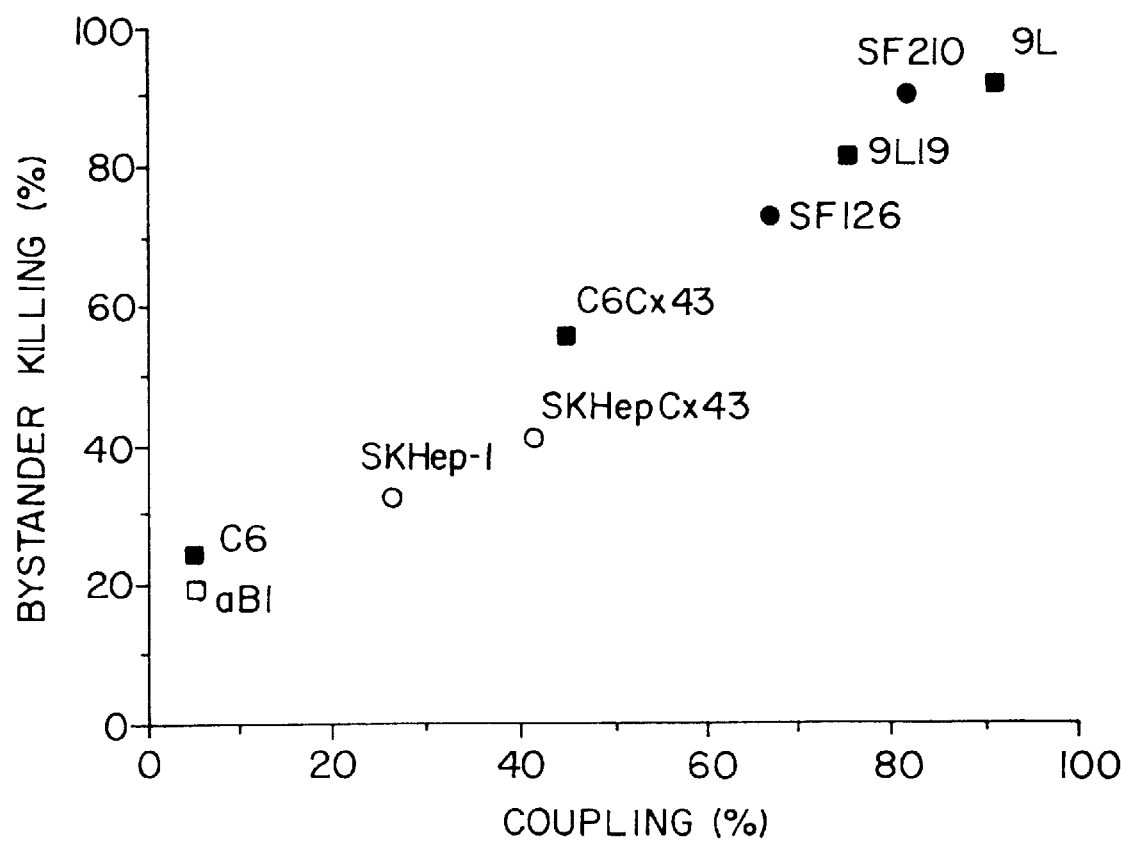
FIG. 2 depicts the bystander killing effect achieved between cells in tissue culture.

The degree of compatibility can be tested by an adaptation of the method described in Fick et al., *Proc. Nat. Acad. Sci. USA*, 92:11071–11075 (1995). Briefly, tumor cell explants are cultured by methods known in the art and labelled with a membrane bound marker such as the fluorescent dye PKH26 (Zynaxis Cell Science, Malvern, Pa.). The connexon protein- and/or adhesion molecule- and/or pro-drug sensitivity-expressing cell type to be used in tumor therapy is labeled with a cytoplasmic marker capable of passing through gap junctions, such as calcein AM (C-1430, Molecular Probes). The cells are co-cultured under conditions that permit the formation of gap junctions between the two cell types. Gap junctional coupling is expressed as the percentage of labeled (e.g., with PKH26) viable (e.g., using dye exclusion assays) tumor cells in which the cytoplasmic marker (e.g., calcein) is also present. FIG. 1 depicts the coupling detected between cells in tissue culture. FIG. 2 illustrates the bystander killing effect achieved between cells in tissue culture, as described in Fick et al. As these figures show, the extent of coupling varies between cell types and may be readily quantified.

If cells derived from different tissues, individuals or species are used, it may be important to suppress or control the host organism's immune response in order to prevent unwanted destruction of the engineered cells.

The engineered cells used herein may also be cell lines that are capable of inducibly generating replication-defective retroviral particles capable of infecting adjacent cells. These particles may encode connexon protein molecules, or pro-drug sensitivity genes, or both. Thus the tumor cells of the tumor wherein the cells were injected may be transduced to themselves express connexon protein and/or a pro-drug sensitivity, and to in turn pass these to surrounding tumor cells.

3. Transduction

There are several well-known methods of introducing nucleic acids into animal cells, any of which may be used in the present invention. These include: calcium phosphate precipitation, fusion of the recipient cells with bacterial protoplasts containing the DNA, treatment of the recipient cells with liposomes containing the DNA, DEAE dextran, receptor-mediated endocytosis, electroporation, microinjection of the DNA directly into the cells, infection with viral vectors, etc.

The present invention also contemplates methods of co-expressing a gene that enhances intercellular communication (e.g., a connexon protein gene) and a gene that encodes either a toxic molecule, a pro-drug activating molecule (such as thymidine kinase) that mediates the production of a gap junction-permeant toxic molecule, or a molecule that can be chemically transformed into a toxic product. The two genes are inserted into separate vectors and are separately introduced into a same host cell, or they are inserted into a same vector and co-introduced in a same host cell.

This co-expression can be performed in vitro or in vivo. In vivo gene transfer methods are known to those of skill in the art. For in vivo administration, pharmaceutical compositions comprising the appropriate vector are preferably administered intratumorly, intraarticularly, intravenously, intraperitoneally, subcutaneously, or intramuscularly. More preferably, the pharmaceutical compositions are administered intratumorly by a bolus injection. For example, see Stadler, et al., U.S. Pat. No. 5,286,634, which is incorporated herein by reference. Intracellular nucleic acid delivery has also been discussed in Straubringer, et al., METHODS IN ENZYMOLOGY, Academic Press, New York. 101:512–527 (1983); Mannino, et al., Biotechniques 6:682–690 (1988); Nicolau, et al., Crit. Rev. Ther. Drug Carrier Syst. 6:239–271 (1989), and Behr, *Acc. Chem. Res.* 26:274–278 (1993).

The methods of the present invention may be practiced in a variety of hosts. Preferred hosts include mammalian species, such as humans, non-human primates, dogs, cats, cattle, horses, sheep, and the like.

The amount of vectors administered will depend upon the particular nucleic acid used, the mode of administration, the disease state being diagnosed; the age, weight, and condition of the patient and the judgement of the clinician; but will generally be between about 0.01 and about 50 mg per kilogram of body weight; preferably between about 0.1 and about 5 mg/kg of body weight or about $10^8$–$10^{10}$ vectors per injection.

4. Detection of expression of connexon protein and selected genes

After a given cell is transduced with a nucleic acid construct that encodes a connexon protein and optionally a drug sensitivity gene, it is important to detect which cells and cell lines express connexon protein and to assess the level of expression of connexon protein or a pro-drug activating molecule in engineered cells. This requires the detection of nucleic acids that encode a connexon protein or a pro-drug activating molecule, and also the detection of the protein gene products.

Nucleic acids and proteins are detected and quantified herein by any of a number of means well known to those of skill in the art. These include analytic biochemical methods such as spectrophotometry, radiography, electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like. The detection of nucleic acids proceeds by well known methods such as Southern analysis, northern analysis, gel electrophoresis, PCR, radiolabeling, scintillation counting, and affinity chromatography.

a. Detection of nucleic acids encoding connexon protein

A variety of methods of specific DNA and RNA measurements and nucleic acid hybridization techniques known to those of skill in the art are useful for detecting and quantifying the presence and expression of connexon protein or pro-drug activating molecules. For example, one method for evaluating the presence of connexon protein DNA in a sample involves a Southern transfer. Southern et al., *J. Mol. Biol.*, 98:503 (1975). Briefly, the digested genomic DNA is run on agarose slab gels in buffer and transferred to membranes. Hybridization is carried out using probes that recognize a connexon protein sequence.

Similarly, a Northern transfer may be used for the detection of connexon protein mRNA in samples of RNA from engineered cells that express the connexon protein gene. In brief, the mRNA is isolated from a given cell sample using an acid guanidinium-phenol-chloroform extraction method. The mRNA is then electrophoresed to separate the mRNA species and the mRNA is transferred from the gel to a nitrocellulose membrane. As with the Southern blots, labeled probes are used to identify the presence or absence of a connexon protein transcript.

The selection of a nucleic acid hybridization format is not critical. A variety of nucleic acid hybridization formats are known to those skilled in the art. For example, common formats include sandwich assays and competition or displacement assays. Hybridization techniques are generally described in "Nucleic Acid Hybridization, A Practical Approach," Ed. Hames, B. D. and Higgins, S. J., IRL Press, 1985.

The sensitivity of the hybridization assays may be enhanced through use of a nucleic acid amplification system which multiplies the target nucleic acid being detected. In vitro amplification techniques suitable for amplifying sequences for use as molecular probes or for generating nucleic acid fragments for subsequent subcloning are known. Examples of techniques sufficient to direct persons of skill through such in vitro amplification methods, including the polymerase chain reaction (PCR) the ligase chain reaction (LCR), Q,β-replicase amplification and other RNA polymerase mediated techniques (e.g., NASBA) are found in Berger, Sambrook, and Ausubel, as well as Mullis et al., U.S. Pat. No. 4,683,202 (1987); *PCR Protocols A Guide to Methods and Applications* (Innis et al. eds), Academic Press Inc., San Diego, Calif. (1990) (Innis); Arnheim & Levinson (Oct. 1, 1990), *C&EN,* 36–47; Kwoh et al., *The Journal Of NIH Research,* 3:81–94 (1991); Kwoh et al., *Proc. Natl. Acad. Sci. USA,* 86:1173 (1989); Guatelli et al., *Proc. Natl. Acad. Sci. USA,* 87:1874 (1990); Lomell et al., *J. Clin. Chem.,* 35:1826 (1989); Landegren et al., *Science,* 241:1077–1080 (1988); Van Brunt, *Biotechnology,* 8:291–294 (1990); Wu and Wallace, *Gene,* 4:560 (1989); Barringer et al., *Gene,* 89:117 (1990), and Sooknanan and Malek, *Biotechnology,* 13:563–564 (1995). Improved methods of cloning in vitro amplified nucleic acids are described in Wallace et al., U.S. Pat. No. 5,426,039. Other methods recently described in the art are the nucleic acid sequence based amplification (NASBA™, Cangene, Mississauga, Ontario) and Q Beta Replicase systems. These systems can be used to directly identify mutants where the PCR or LCR primers are designed to be extended or ligated only when a select sequence is present. Alternatively, the select sequences can be generally amplified using, for example, nonspecific PCR primers and the amplified target region later probed for a specific sequence indicative of a mutation.

Oligonucleotides for use in in vitro amplification methods, for use as gene probes, or as inhibitor components are typically synthesized chemically according to the solid phase phosphoramidite triester method described by Beaucage and Caruthers, *Tetrahedron Letts.,* 22(20):1859–1862 (1981), e.g., using an automated synthesizer, as described in Needham-VanDevanter et al., *Nucleic Acids Res.,* 12:6159–6168 (1984). Purification of oligonucleotides, where necessary, is typically performed by either native acrylamide gel electrophoresis or by anion-exchange HPLC as described in Pearson and Regnier, *J. Chrom.,* 255:137–149 (1983). The sequence of the synthetic oligonucleotides can be verified using the chemical degradation method of Maxam and Gilbert (1980) in Grossman and Moldave (eds.) Academic Press, New York, *Methods in Enzymology,* 65:499–560.

An alternative means for determining the level of expression of connexon protein is in situ hybridization. In situ hybridization assays are well known and are generally described in Angerer et al., *Methods Enzymol.,* 152:649–660 (1987). In an in situ hybridization assay cells are fixed to a solid support, typically a glass slide. If DNA is to be probed, the cells are denatured with heat or alkali. The cells are then contacted with a hybridization solution at a moderate temperature to permit annealing of connexon protein-specific probes that are labelled. The probes are preferably labelled with radioisotopes or fluorescent reporters.

b. Detection of connexon protein gene products in engineered cells

The expression of connexon protein may be detected or quantified by a variety of methods. Preferred methods involve the use of specific antibodies.

Methods of producing polyclonal and monoclonal antibodies are known to those of skill in the art. See, e.g., Coligan (1991), *Current Protocols in Immunology,* Wiley/Greene, NY; and Harlow and Lane (1989), *Antibodies: A Laboratory Manual,* Cold Spring Harbor Press, NY; Stites et al. (eds.) *Basic and Clinical Immunology* (4th ed.) Lange Medical Publications, Los Altos, Calif., and references cited therein; Goding (1986), *Monoclonal Antibodies: Principles and Practice* (2d ed.) Academic Press, New York, N.Y.; and Kohler and Milstein, *Nature,* 256:495–497 (1975). Such techniques include antibody preparation by selection of antibodies from libraries of recombinant antibodies in phage or similar vectors. See, Huse et al., *Science,* 246:1275–1281 (1989); and Ward et al., *Nature,* 341:544–546 (1989). Specific monoclonal and polyclonal antibodies and antisera will usually bind with a $K_D$ of at least about 0.1 mM, more usually at least about 1 $\mu$M, preferably at least about 0.1 $\mu$M or better, and most typically and preferably, 0.01 $\mu$M or better.

The presence of a connexin polypeptide (including peptide or enzymatic digestion product) in a sample may be detected and quantified using Western blot analysis. The technique generally comprises separating sample products by gel electrophoresis on the basis of molecular weight, transferring the separated proteins to a suitable solid support, (such as a nitrocellulose filter, a nylon filter, or derivatized nylon filter), and incubating the sample with labeling antibodies that specifically bind to the analyte protein. The labeling antibodies specifically bind to analyte on the solid support. These antibodies are directly labeled, or alternatively are subsequently detected using labeling agents such as antibodies (e.g., labeled sheep anti-mouse antibodies where the antibody to an analyte is a murine antibody) that specifically bind to the labeling antibody.

C. Administration of modified cells to cancer patients

1. Selection of patients

The patients to be treated by the methods of the invention are cancer patients. The claimed methods are effective against a range of different cancer types. Preferably the cancer is a tumor-forming cancer. For example, many solid tumors are amenable to treatment using the claimed invention. These tumors include but are not limited to tumors of neuroectodermal derivation (e.g., glioma), carcinomas (e.g., colon cancer, ovarian cancer), and tumors of mesodermal origin (e.g., sarcomas).

2. Pre-testing for efficacy against a particular cancer

In order to assess how well the methods of the invention may be expected to work, the clinician can pre-test the efficacy of the treatment of a particular tumor type either in vitro or in vivo.

For in vitro tests, cells derived from the tumor are grown in tissue culture. The method described in Fick et al. is used to assess the efficacy of using a particular engineered cell line to transfer therapeutic molecules to the tumor-derived cells. The growth inhibiting effect may be assessed using a number of commonly used assays, such as cell counts, or radioactive thymidine incorporation, or a methylcellulose assay (Lunardi-Iskandar et al., *Clin. Exp. Immunol.*, 60:285–293 (1985)).

3. Methods of administration and dosages

Administration of cells to a cancer patient can be achieved in various ways known to skilled practitioners. The cells can be injected intratumorly: the tumor, the placement of the needle and release of the contents of the syringe may be visualized either by direct observation (for easily accessible tumors such as surface tumors or tumors easily exposed by surgical techniques), by endoscopic visualization, or by electromagnetic imaging techniques such as ultrasound, magnetic resonance imaging (MRI), CT scans. The cells can also be administered via injection into the bloodstream using a cannula or catheter; the vein or artery is selected to maximize delivery of cells to the tumor or affected tissue. The cells can be injected into cerebro-spinal fluid (i.e., into intracisternal, intraventricular, intrathecal or subarachnoid compartments). In cystic or vesicular tumors or tissues, the cells may be delivered intracystically or intravesicularly.

It is contemplated that the cells will be administered under the guidance of a physician. The concentration and number of cells to be administered at a given time and to a given patient will vary from $10^5$ to $10^{10}$ cells per patient. Generally, the number of cells to be administered is the amount necessary to reduce cancer cell growth and/or to destroy cancer cells and/or preferably to eradicate the cancer. The exact number is a function of the size and compactness (or diffuseness) of the particular transformed cell mass to be treated, and the distance or accessibility of the tissue to be treated from the point of administration of the cells. More than one administration may be necessary. As with any medical treatment, the supervising physician will monitor the progress of the treatment, and will determine whether a given administration is successful and sufficient, or whether subsequent administrations are needed.

The injected cells and cells junctionally coupled to them may be destroyed by administration of a pro-drug to the patient that will target for destruction the injected cells and cells that are junctionally coupled to them. For example, the enzyme cytosine deaminase converts 5-fluorocytosine ("5FC") into the lethal metabolite 5-fluorouracil ("5FU"). Cells that express cytosine deaminase, when exposed to 5FC, will die as a result of the formation of 5FU. Cells that do not express the deaminase but that are junctionally coupled to deaminase-expressing cells will also die. Another gene that confers drug sensitivity upon a host cell is the thymidine kinase gene, which confers sensitivity to GCV. Administration of the pro-drug may be local or systemic and may be achieved by any of the methods for administration of the cells.

4. Monitoring treatment

Tumor regression and other parameters of successful treatment are assessed by methods known to persons of skill in the art. This includes any imaging techniques that are capable of visualizing cancerous tissues (e.g., MRI), biopsies, methods for assessing metabolites produced by the cancer tissue or affected tissue in question, the subjective well-being of the patient, etc.

EXAMPLES

Example 1

This example shows that in vivo Ganciclovir (GCV) tumor toxicity which results from exposure of tumor cells to fibroblast cell lines that express the thymidine kinase (tk) gene increases as a function of ability to carry out gap junction-mediated intercellular communication.

The HSV-tk gene encodes an activity capable of converting the non-cytotoxic molecule GCV to a cytotoxic one. Cells that are exposed to harmful levels of the cytotoxic molecule die.

The HSV-tk gene was stably cloned into a PA/317 fibroblasts as described in *Mol. Cell. Biol.* 6:2895–2902 (1986) and *New Eng. J. Med.* 232:570–578 (1990). Athymic (immune-incompetent) BALB/C mice were injected subcutaneously with mixtures of: 1) $1\times10^7$ tumor cells known to have either high (9L glial tumor cells) or low (C6 glial tumor cells) levels of gap junction mediated intercellular transport, and 2) $1\times10^7$ immortalized mouse fibroblasts (PA317 cells) engineered to express HSV-tk. The mixtures of inoculated cells were allowed to grow into tumors over a period of 7–14 days (the time for detectable tumor formation varied depending on the identity and number of injected cells). The tumor-bearing animals were then treated for 7 days with GCV (25 mg/kg, BID) or with phosphate buffeted saline (PBS). Tumor size was periodically monitored.

Figure 3:
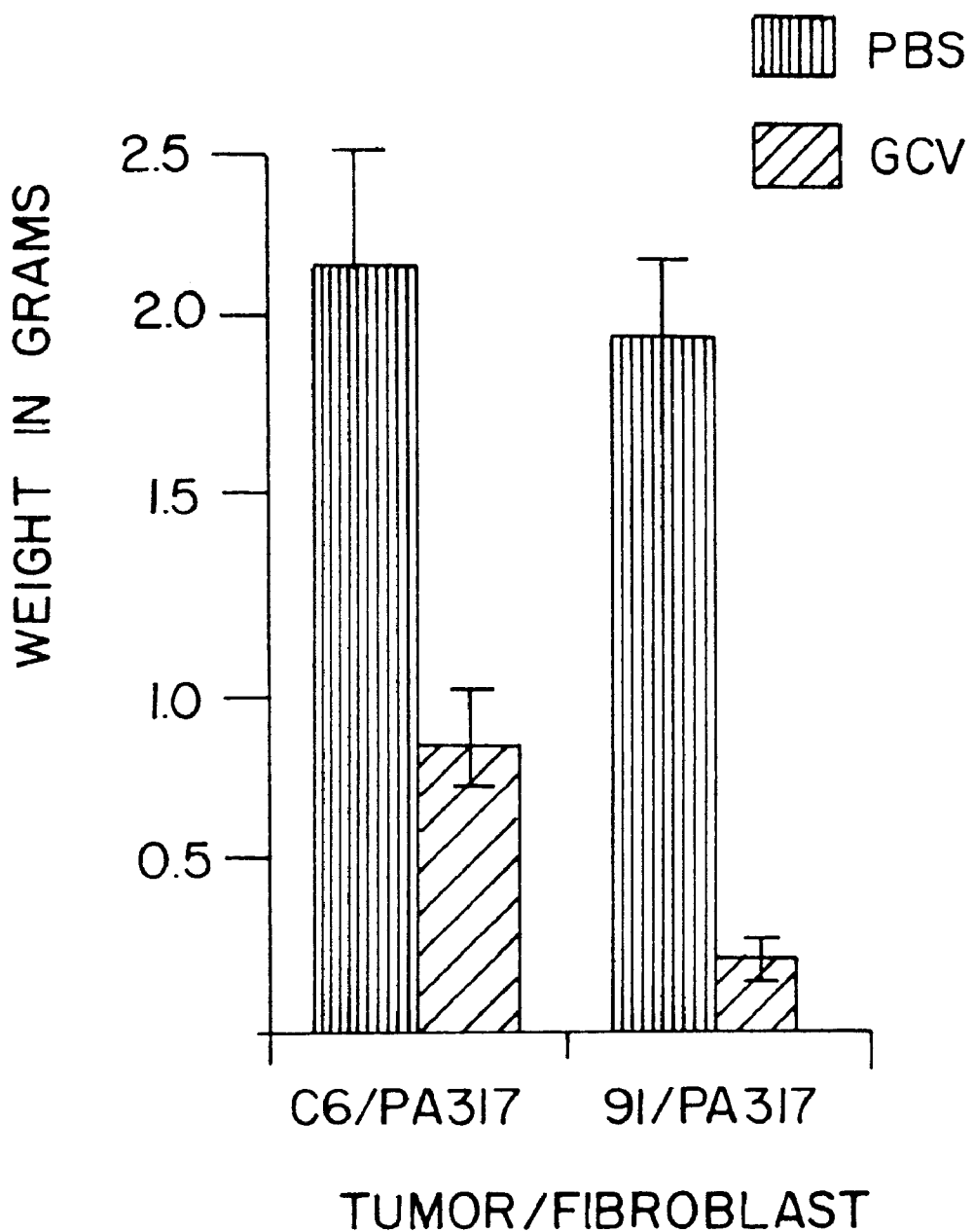
FIG. 3 illustrates that in vivo Ganciclovir (GCV) tumor toxicity increases as a function of ability to carry out gap junction-mediated intercellular communication.

14 days following the initiation of GCV treatment the tumors were removed. FIG. 3 summarizes the average weight of tumors following their removal. As can be appreciated in FIG. 3, the tumors from animals exposed to 9L cells and GCV were significantly smaller than the tumors from animals exposed to 6C cells and GCV. Thus, tumor toxicity was greater in tumors with higher levels of gap junction mediated intercellular transport. In other words, tumors consisting of cells known to be able to avidly exchange molecules with the fibroblasts expressing HSV-tk (9L cells) and thereby easily pass cytotoxic molecules through gap junctions were more effectively killed by bystander effect in vivo than cells which did not as effectively form gap junctions.

Example 2

Example 2 demonstrates that injecting HSVtk-expressing fibroblasts into pre-existing tumors is effective to decrease tumor mass, and that the cytotoxicity is greater in tumors with higher gap junction-mediated intercellular transport.

5 athymic (immuno-incompetent) mice were injected subcutaneously with $1\times10^7$ tumor cells known to have either high (9L glial tumor cells) or low (C6 glial tumor cells) levels of gap junction mediated intercellular transport. $1\times10^7$ HSV-tk$^+$ fibroblasts (PA317 cells) were injected into the center of tumors that were formed. GCV therapy (25 mg/kg, BID) was commenced 24 hours later and continued for 7 days. 14 days following the initiation of GCV treatment the tumors were removed and weighed.

Figure 4:
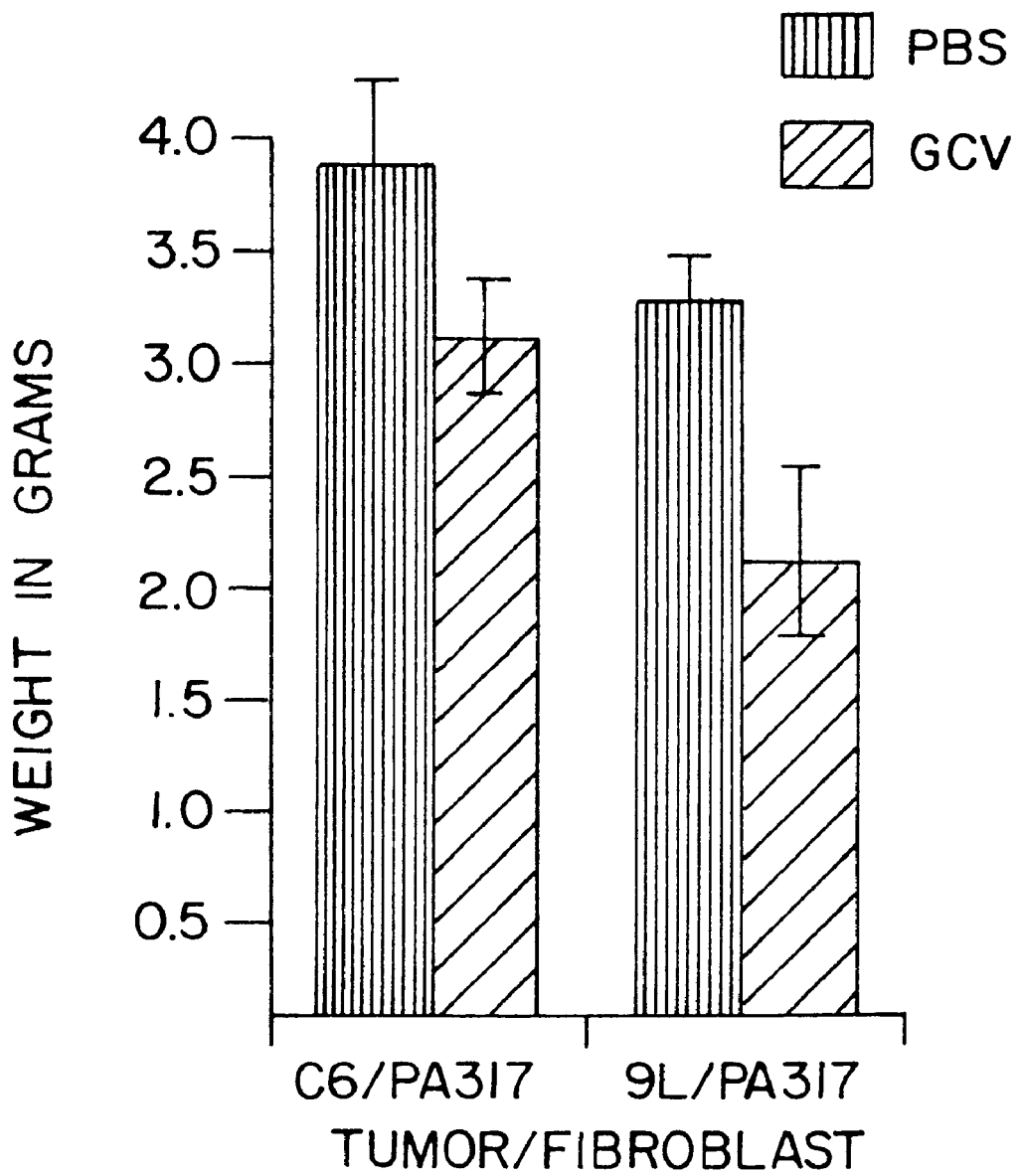
FIGS. 4A–D illustrates that injecting HSVtk-expressing fibroblasts into pre-existing tumors is effective to decrease tumor mass, and that the toxicity is greater in tumors with higher gap junction mediated intercellular transport.

FIG. 4 illustrates that the effect of GCV treatment was greater in 9L cells. These findings indicate the importance of gap junction mediated transport for the bystander killing of tumor cells. Established tumors of cells known to be able to avidly exchange molecules with the fibroblasts expressing HSV-tk and thereby easily pass cytotoxic molecules through gap junctions (9L cells) were more effectively killed by bystander effect than are cells which did not as effectively form gap junctions (C6 cells) under conditions which mimic closely the conditions under which this therapy would be used clinically.

Example 3

This example illustrates that the expression of connexon proteins such as connexin43 modulates GCV tumor toxicity.

To evaluate the role of connexin and gap junctions in the in vivo GCV tumor cytotoxicity, HSV-tk was expressed in fibroblast cells which were derived from a mouse in which both copies of the connexin43 gene had been deleted from its genome (genetic constitution), as described in Reaume et al., *Science* 267:1831–4 (1996). We then examined the ability of these connexin43⁻ fibroblasts and comparable fibroblasts derived from normal mice to mediate intercellular gap junction mediated transport.

Fibroblasts from connexin43⁻ mice or wild type mice were labeled with a cytoplasmic fluorescent dye, Calcein AM. 9L and HT1335 tumor cells were labeled with a membrane-bound fluorescent dye, PKH26. $10^6$ Calcein AM-labeled fibroblasts and $10^6$ PKH26-labeled tumor cells were seeded in 6 well plates and incubated for 3.5 hrs. Cells were washed with Cu++/Mg++-free phosphate buffered saline (PBS), trypsinized, centrifuged, and resuspended in PBS containing 0.3% FBS, 0.03 μg/ml propidium iodide and 0.3 μg/ml Hoechst 33342. After 30 min., cells were analyzed by flow cytometry using a dual laser system. Calcein and PKH26 emissions were excited with a 488 nm argon laser and collected through 525/25 and 575/25 nm band pass filters, respectively. Hoechst 33342 emissions were excited with a 354/363 nm argon laser and collected through a 470/25 nm band pass filter. Data from 20,000 cells were acquired from each sample. Dead cells were excluded by gating based on cellular forward light scatter and propidium iodide fluorescence. Fluorescence signals were measured on a four decades logarithmic scale and cell phases were analyzed on a 1024 channel linear scale. Coupling was detected by the identification of viable PKH26-labeled tumor cells in which calcein fluorescence was also detected.

Figure 5:
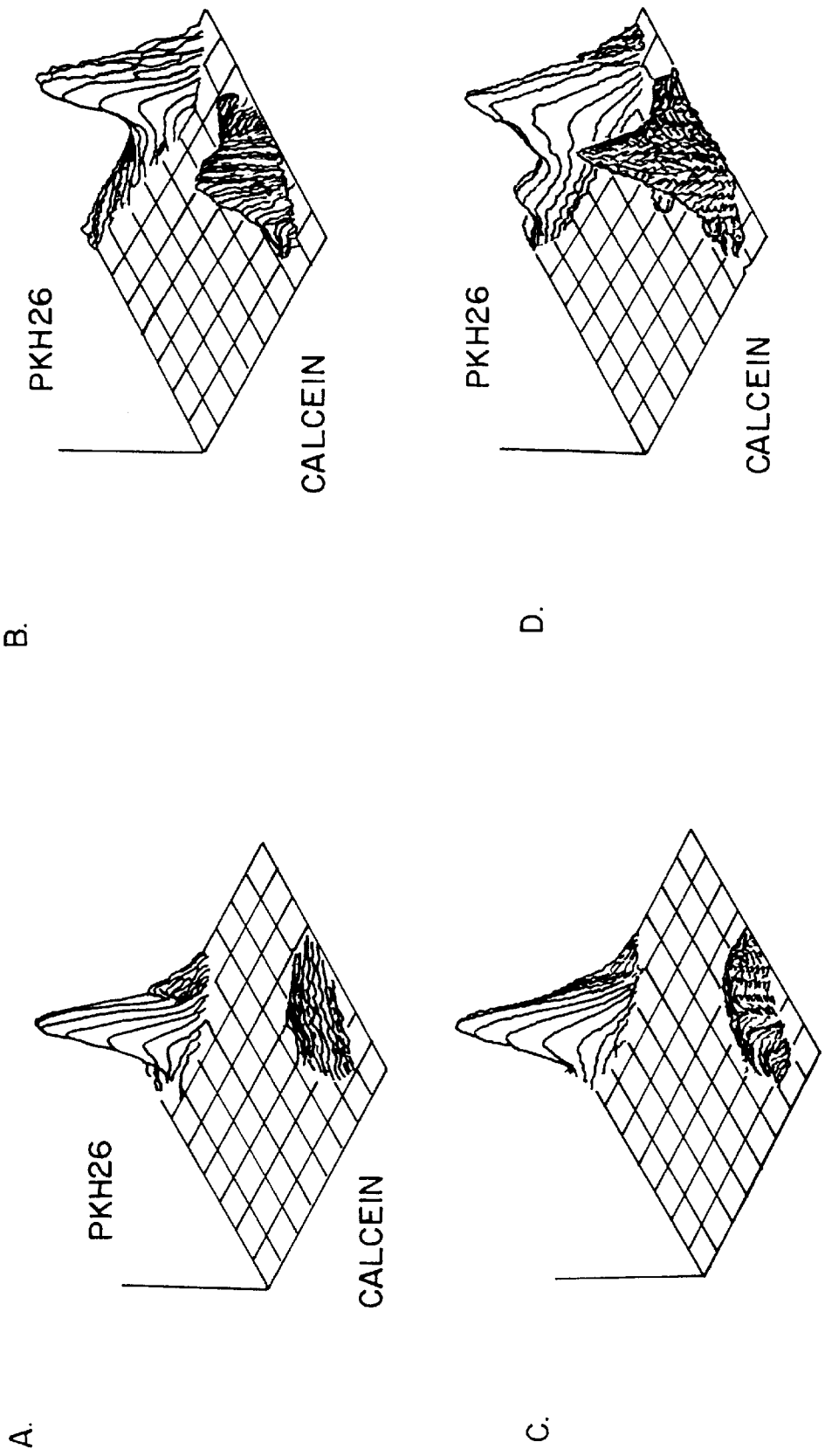
FIG. 5 illustrates that the expression of connexon proteins such as connexin43 modulates GCV tumor toxicity.

FIG. 5 is a composite of the results obtained from experiments in which different cells were labeled, incubated and evaluated for coupling. The x,y axis demarcations are in arbitrary FACS units indicating the intensity of fluorescence of the indicated dyes and the z axis marks the relative number of cells characterized by a specific fluorescence pattern. The pattern observed for thr following cell types were examined in the experiments shown in FIG. 5: Panel A) connexin43⁻ fibroblasts and 9L tumor cells, Panel B) wild-type fibroblasts and 9L tumor cells. Panel C) connexin43⁻ fibroblasts and HT1335 tumor cells, Panel D) wildtype fibroblasts and HT1335 tumor cells.

These results indicate the connexin43⁻ fibroblasts do not mediate gap junction intercellular transport with these tumor cell lines (Panel A, C), from rat (9L) or from human (HT1335), whereas wildtype fibroblasts do (Panels B, D). Since the only difference between the wildtype and connexin43⁻ fibroblasts is the absence of a connexin43 gene, this indicates that this genes is required for gap junction mediated transport in these cells. These findings demonstrate that expression of connexin43 is required for bystander-mediated killing and an effective prodrug activation gene therapy. Connexin43⁻ fibroblasts would not be effective treatment vehicles for gene therapy strategies that depended upon bystander cell killing to be effective.

Example 4

Example 4 illustrates that the in vivo tumor toxicity observed in Examples 1 and 2 involves the expression of connexon proteins such as connexin43. Here, the efficacy of GCV to inhibit tumor growth of 9L tumor cell mouse xenografts grown in the presence of HSV-TK⁺ fibroblasts which express connexin43 was compared to the efficacy of HSV-TK⁺, connexin43⁻ fibroblasts.

5 athymic (immuno-incompetent) mice were injected subcutaneously with mixtures of $1 \times 10^7$ 9L tumor cells and either immortalized connexin43⁻ mouse fibroblasts engineered to express HSV-tk (5 mice) or immortalized mouse fibroblasts from normal mice which express connexin 43 and had also been engineered to express HSV-tk (5 mice). The inoculated cells were allowed to grow into tumors. The tumor-bearing animals were treated with GCV (25 mg/kg) for 7 days. Tumor size was monitored and 14 days following the initiation of GCV treatment the tumors were removed. In a parallel experiment, animals injected with a mixture of $1 \times 10^7$ 9L tumor cells and with immortalized connexin43⁻ mouse fibroblasts engineered to express HSV-tk were mock-treated with sham injections of phosphate buffeted saline (PBS) lacking GCV.

Figure 6:
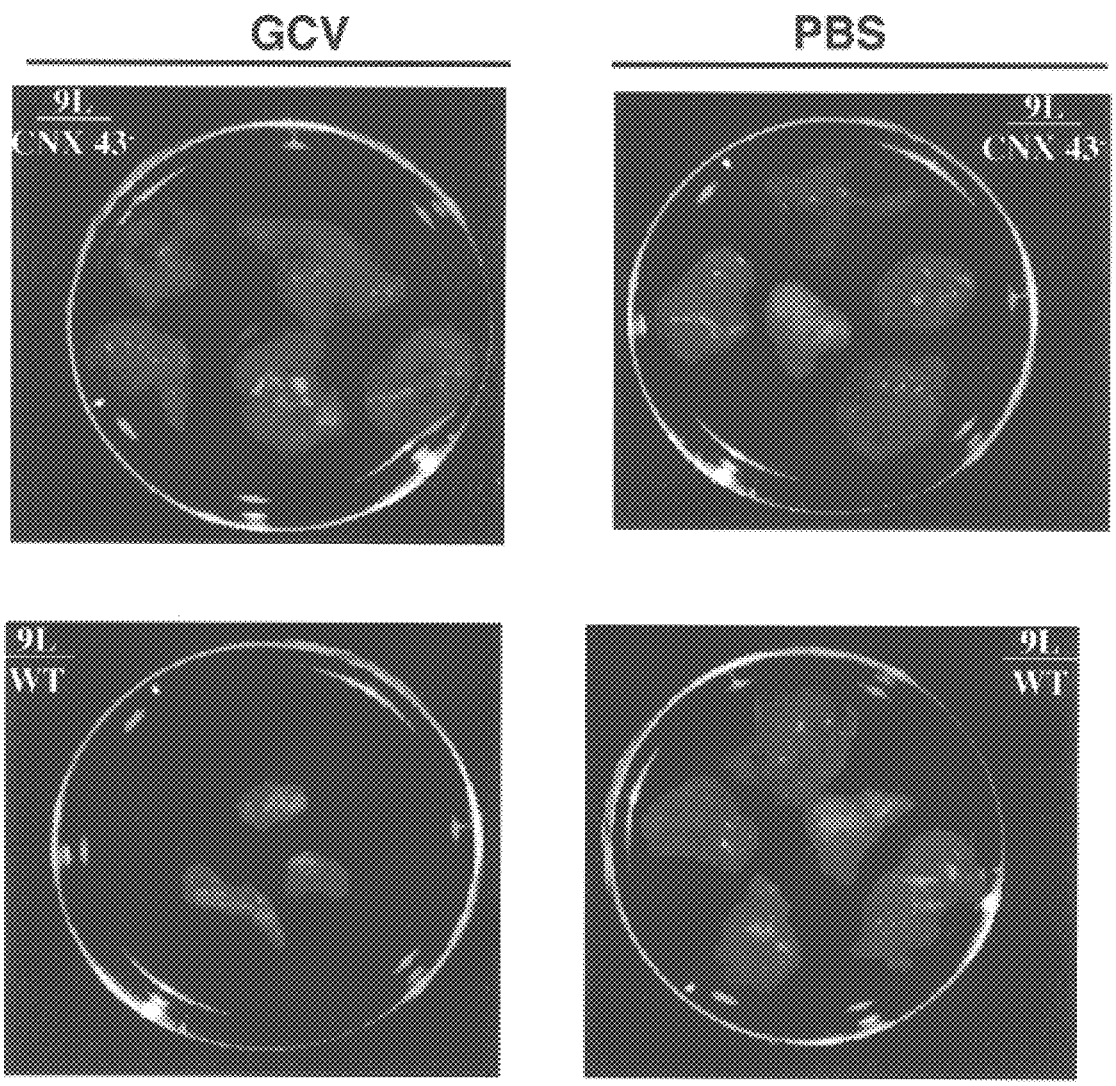
FIG. 6 summarizes the effects of regulating connexon protein expression on GCV tumor toxicity in vivo.

GCV administration had a highly therapeutic effect against tumors which contained fibroblasts with normal gap junction (normal connexin 43 genes), but was not effective in treating tumors consisting of 9L cells and HSV-tk⁺ fibroblasts in which the connexin genes had been deleted (FIG. 6). Of the 5 animals with tumors consisting of 9L cells and HSV-tk⁺ fibroblasts expressing connexin43, only 3 animals still had detectable tumors when examined 7 days after the completion of GCV therapy. These tumors had an average weight of 0.63 g. A matched control group of 5 animals which received sham injections of phosphate buffeted saline (PBS) instead of GCV all had tumors 7 days after the completion of this "sham treatment". The tumors had an average weight of 4.35 g.

Two other groups of 5 animals inoculated with mixtures of 9L cells and HSV-tk⁺ fibroblasts derived from cells lacking any connexin43 genes were identically treated. Those which did not receive GCV all had tumors, and the average weight of these tumors was 5.68 g. All 5 animals in the group inoculated with 9L cells and connexin43⁻ fibroblasts also had tumors, even after 7 days of GCV treatment; the tumors had an average weight of 5.43 g.

Thus, tumors consisting of cells known to be able to avidly exchange molecules with the fibroblasts expressing HSV-tk and thereby easily pass cytotoxic molecules through gap junctions were more effectively killed by bystander effect in vivo than cells which ineffectively form gap junctions; namely, HSV-tk⁺/connexin43⁻ fibroblasts. These findings indicate that connexon gene expression is required for gap junction mediated intercellular transport which mediates the bystander killing of tumor cells in vivo, and contributes to the optimization of gene therapy strategies such as viral pro-drug activation which require bystander cell killing to be efficacious.

Example 5

In one embodiment of the invention, patients diagnosed as having metastatic ovarian cancer of the peritoneal cavity are treated as follows:

1. Engineered cells

Commercially obtained NIH3T3 cells are genetically engineered to express thymidine kinase and connexin 43 as follows: The vector pcDNA3-HSVtk, which contains a cDNA clone encoding the Herpes simplex virus thymidine kinase (HSV-tk) gene is constructed by standard technologies in pcDNA3 obtained from Invitrogen (San Diego, Calif.). pBluescript-HSV-TK DNA is digested with BamH1 restriction enzyme and the fragment containing the HSV-TK coding region is isolated. The vector pcDNA (obtained from Invitrogen) containing a neomycin resistance gene is digested with restriction enzymes BamH1 and the HSV-TK coding fragment is ligated into the BamH1 site of the expression vector. The resulting pcDNA3-HSVtk vector is cloned by the standard technologies. See *Molecular Cloning—A Laboratory Manual* (2nd ed.) Vol. 1–3, Cold Spring Harbor Laboratory, Cold Spring Harbor Press, N.Y., (Sambrook); and F. M. Ausubel et al., *Current Protocols in Molecular Biology,* eds., Current Protocols, a joint venture between Greene Publishing Associates, Inc. and John Wiley & Sons, Inc. (1994 Supplement) (Ausubel). The plasmid vector pBluescript containing the recombinant cDNA encoding chicken connexin43 (obtained from Dr. Eric Beyer Washington University) is digested with restriction enzyme EcoRI and the fragment containing the connexin43 coding region is isolated. The vector pMEP4 which contains the hygromycin resistance gene for selection is digested in the restriction enzyme EcoRI. The connexin43 fragment is ligated into the EcoRI site, and the resulting pMEP4-Cx43 vector is cloned. This pMEP4-Cx43 encodes both connexin43 and a hygromycin resistance gene.

NIH3T3 cells are transfected with the pcDNA3-HSVtk vector using the calcium phosphate technique described in *Molecular Closing—A Laboratory Manual* (2nd ed.) Vol. 1–3, Cold Spring Harbor Laboratory, Cold Spring Harbor Press, N.Y. (Sambrook); and Ausubel, F. M. et al., *Current Protocols in Molecular Biology,* eds., Current Protocols, a joint venture between Greene Publishing Associates, Inc. and John Wiley & Sons, Inc. (1994 Supplement) (Ausubel). Transfected cell clones are selected in neomycin. Individual clones are tested for the expression of the tk cDNA by Northern and Southern blots and by immunoassays using anti-thymidine kinase antibodies. Thymidine kinase expression is also determined by testing sensitivity to GCV, as described by Fick et al.

Selected NIH3T3-tk clones generated above are then transfected with the pMEP4-Cx43 vector as described above. NIH3T3-tk-cx clones are obtained by incubating the cells in neomycin and hygromycin. Individual NIH3T3-tk-cx clones are tested for the expression of the TK and connexin cDNA by Northern and Southern blots and by immunoassays using anti-thymidine kinase and anti-connexin 43 antibodies. Thymidine kinase expression is also determined by testing sensitivity to GCV, as described by Fick et al. Likewise, PA317 cells, which are NIH3T3 cells expressing HSV-tk, can be transfected with the above described pMEP-Cx43, selected in hygromycin, evaluated for expression of tk and connexin, and tested for GCV sensitivity as described above.

Clones having a heightened ability to form functional gap junctions can be identified by the method described in Fick et al. using appropriate cells as the assay partner, such as C6 or U87 cells. The ability of these clones to mediate bystander killing are determined by the method described in Fick et al. Cells with the highest activity in the bystander killing assay are used for in vivo cancer treatments.

Freshly made or cryopreserved NIH-TK-Cx43 or PA317-Cx43 clones exhibiting a high bystander killing ability are injected directly into the peritoneal cavity of a patient either by peritoneal injection or under direct visualization with peritonoscopy. The diagnosis of a tumor is made by any of the following methods: evaluation of peritoneal fluid, peritoneal washes, or biopsy of peritoneal tumor implants. The presumptive diagnosis is confirmed at the time of surgery by a pathologist who evaluates a specimen removed by the surgeon or oncologist who collected the pathological specimen. The injected, engineered cells are allowed to establish contact with the tumor cells for an appropriate time period (for example, 4–72 hours.) The patient is then treated with the pro-drug GCV intravenously. Inhibition of tumor growth can be monitored by serial evaluations of the peritoneal cavity by MRI scanning, direct visualization by peritonoscopy, or examination of peritoneal fluid or wash fluid for malignant cellular elements.

Example 6

In another embodiment of the invention, patients diagnosed as having an intracranial meningioma are treated as follows:

1. Engineered cells

Commercially obtained PA317 cells which are genetically modified 3T3 cells that express thymidine kinase are engineered to express connexin 43 as follows: The plasmid vector pBluescript containing the recombinant cDNA encoding chicken connexin43 (obtained from Dr. Eric Beyer, Washington University) is digested with restriction enzyme EcoRI, and the fragment containing the connexin43 coding region is isolated. The vector pMEP4 which contains the hygromycin resistance gene for selection is digested with the restriction enzyme EcoRI. The connexin43 fragment is ligated into the EcoRI site, and the resulting pMEP4-Cx43 vector is cloned. This pMEP4-Cx43 encodes both connexin43 and a hygromycin resistance gene.

PA317 cells are transfected with the pMEP-4-Cx43 vector using the calcium phosphate technique described in *Molecular Closing—A Laboratory Manual* (2nd ed.) Vol. 1–3, Cold Spring Harbor Laboratory, Cold Spring Harbor Press, N.Y. (Sambrook); and Ausubel, F. M. et al., *Current Protocols in Molecular Biology,* eds., Current Protocols, a joint venture between Greene Publishing Associates, Inc. and John Wiley & Sons, Inc. (1994 Supplement) (Ausubel). Transfected cell clones are selected in hygromycin. Thymidine kinase expression is also determined by testing sensitivity to GCV, as described by Fick et al.

Individual PA317-CX43 clones are tested for the expression of the connexin43 cDNA by Northern and Western blots and by immunoassays using anti-connexin 43 antibodies. Thymidine kinase expression is also determined by testing sensitivity to GCV, as described by Fick et al.

Clones having a heightened ability to form functional gap junctions are identified by the method of Fick et al., using as the assay partner a human glioma tumor cell line with low coupling (serving as a sensitive monitor) such as SF295. The ability of these clones to mediate bystander killing are determined by the method described in Fick et al. Cells with the highest activity in the bystander killing assay are used for in vivo cancer treatments.

2. Treatment of patients

Freshly made or cryopreserved NIH3T3-TK-CX clones exhibiting a high bystander killing ability are injected directly into the brain tumors of a patient under direct visualization at the time of surgery. The diagnosis of a tumor is made by any neuroimaging modality which allows the localization and characterization of a tumor. The presumptive diagnosis is confirmed at the time of surgery by a pathologist who evaluates a surgical specimen removed by the surgeon. The injected engineered cells are allowed to establish contact with the tumor cells for an appropriate time (for example, 4–72 hours). The patient is then treated with the pro-drug GCV intravenously. Inhibition of tumor growth can be monitored by serial MRI scans.

We claim:

1. A method of inhibiting the growth of tumor cells in a mammal, which method comprises:

a) providing engineered non-tumorigenic cells that express a first heterologous nucleic acid that encodes a connexon protein and a second heterologous nucleic acid that encodes a pro-drug activating molecule that converts a non-toxic substrate to a toxic product, and b) directly administering to a solid tumor the cells of step a, then c) exposing the engineered and tumor cells to a therapeutic amount of a non-toxic substance that is converted to a toxic product in cells that express the pro-drug activating molecule, wherein the cell growth of the tumor cells exposed to the toxic product is inhibited.

2. A method according to claim 1, wherein the non-tumorigenic engineered cells are selected from the group that consists of engineered non-tumorigenic fibroblasts, epithelial cells, endothelial cells, bone cells, keratinocytes, and irradiated, engineered non-tumorigenic cells derived from tumors.

3. A method according to claim 2, wherein the non-tumorigenic engineered cells are PA317 fibroblasts.

4. A method according to claim 1, wherein the tumor cells are selected from the group of tumor cells that consist of embryonal tumors, sarcomas, carcinomas, and tumors of neuroectodermal origin.

5. A method according to claim 1, wherein the tumor cells are selected from the group of human tumor cells that consist of glioma cells, colon carcinoma cells, prostate cancer cells, breast cancer cells, lung cancer cells, kidney cancer cells, kidney cancer cells, osteosarcoma cells, and neuroblastoma cells.

6. A method according to claim 1, wherein the pro-drug activating molecule is selected from the group that consists of thymidine kinase, cytosine deaminase, and β-glucosidase.

7. A method according to claim 1, wherein the connexon protein is selected from the group that consists of connexin 26, connexin 32, connexin 43 and connexin 45.

8. A method according to claim 1, wherein the connexon protein is ductin.

9. A method according to claim 1, wherein the engineered cell and the target cell are from the same individual.

10. A composition comprising an engineered non-tumorigenic cell that expresses a first heterologous nucleic acid that encodes a connexin and a second heterologous nucleic acid that encodes a pro-drug activating molecule that converts a non-toxic substrate to a toxic metabolite.

11. A composition of claim 10, wherein the engineered non-tumorigenic cell is selected from the group that consists of engineered fibroblasts, epithelial cells, endothelial cells, bone cells, keratinocytes, and irradiated, engineered non-tumorigenic cells derived from tumors.

* * * * *